(12) United States Patent
Alley et al.

(10) Patent No.: US 7,837,980 B2
(45) Date of Patent: Nov. 23, 2010

(54) PARTIALLY LOADED ANTIBODIES AND METHODS OF THEIR CONJUGATION

(75) Inventors: Stephen C. Alley, Seattle, WA (US);
Michael Torgov, Hamden, CT (US);
Michael Sun, Bothell, WA (US)

(73) Assignee: Seattle Genetics, Inc., Bothell, WA (US)

( * ) Notice: Subject to any disclaimer, the term of this patent is extended or adjusted under 35 U.S.C. 154(b) by 413 days.

(21) Appl. No.: 10/591,743

(22) PCT Filed: Mar. 2, 2005

(86) PCT No.: PCT/US2005/007239
§ 371 (c)(1),
(2), (4) Date: Aug. 13, 2008

(87) PCT Pub. No.: WO2005/084390
PCT Pub. Date: Sep. 15, 2005

(65) Prior Publication Data
US 2009/0010945 A1    Jan. 8, 2009

Related U.S. Application Data

(60) Provisional application No. 60/549,476, filed on Mar. 2, 2004.

(51) Int. Cl.
| | |
|---|---|
| A61K 51/10 | (2006.01) |
| A61K 39/395 | (2006.01) |
| C07K 16/18 | (2006.01) |
| C07K 16/22 | (2006.01) |
| C07K 16/28 | (2006.01) |
| C12P 21/08 | (2006.01) |

(52) U.S. Cl. .................. 424/1.49; 424/1.53; 424/178.1; 530/391.1; 530/391.5; 530/391.7; 530/405; 530/408; 530/412; 530/413

(58) Field of Classification Search .................. None
See application file for complete search history.

(56) References Cited

U.S. PATENT DOCUMENTS

| 6,884,869 B2 | 4/2005 | Senter et al. | |
|---|---|---|---|
| 2004/0018194 A1 | 1/2004 | Francisco et al. | |
| 2005/0152894 A1 | 7/2005 | Krummen et al. | |
| 2005/0175619 A1 | 8/2005 | Duffy et al. | |
| 2005/0238649 A1* | 10/2005 | Doronina et al. | 424/178.1 |
| 2006/0074008 A1 | 4/2006 | Senter et al. | |
| 2006/0120959 A1* | 6/2006 | De Haen et al. | 424/1.49 |
| 2006/0210526 A1 | 9/2006 | Brocchini et al. | |

FOREIGN PATENT DOCUMENTS

| WO | WO 2006/034488 A2 | 3/2006 |
|---|---|---|
| WO | WO 2006/065533 A2 | 6/2006 |
| WO | WO 2006/065533 A3 | 6/2006 |

OTHER PUBLICATIONS

Doronina et al, Nature Biotechnology 21(7): 778-941, Jul. 2003.*
Sears et al, Proc Nat Acad USA 72(1): 353-357, Jan. 1975.*
Del Rosario, R. et al., "Sulfhydryl Site-Specific Cross-Linking and Labeling of Monoclonal Antibodies by a Fluorescent Equlibrium Transfer Alkylation Cross-Link Reagent," *Bioconjugate Chem.*, 1990, 1, pp. 51-59.
Junutula, J. R. et al., "Rapid identification of reactive cyseteine residues for site-specific labeling of antibody-Fabs", *Journal of Immunological Method*, 2008, 332, pp. 41-52.
Wilbur D. et al., "Monoclonal Antibody Fab' Fragment Cross-Linking Using Equlibrium Transfer Alkylation Reagents. A Strategy for Site-Specific Conjugation of Diagnostic and Therapeutic Agents with F(ab')$_2$ Fragments," *Bioconjugate Chem.*, 1994, 5, pp. 220-235.
Doral et al., "Role of Inter-Heavy and Light Chain Disulfide Bonds in the Effector Functions of Human Immunoglobulin IgG1," *Molecular Immunology*, 29(12):1487-1491 (1992).
Francisco et al., "cAC10-vcMMAE, an anti-CD30-monomethyl auristatin E conjugate with potent and selective antitumor activity," *Blood*, 102(4):1458-1465 (Aug. 15, 2003).
Gillies et al., "Antigen binding and biological activities of engineered mutant chimeric antibodies with human tumor specificities," *Hum. Antibod. Hybridomas*, 1(1):47-54 (1990).
Hamann et al., "Gemtuzumab Ozogamicin, A Potent and Selective Anti-CD33 Antibody—Calicheamicin Conjugate for Treatment of Acute Myeloid Leukemia," *Bioconjugate Chem.*, 13:47-58 (2002).
Lyons et al., "Site-specific attachment to recombinant antibodies via introduced surface cysteine residues," *Prot. Eng.*, 3(8):703-708 (1990).
Oi et al., "Chimeric Antibodies," *BioTechniques*, 4(3):214-221 (1986).
Product description of Mylotarg® (gemtuzumab ozogamicin for Injection), by Wyeth Pharmaceuticals, Inc., Jul. 2004 revision, pp. 1-19.
Qu et al., "Carbohydrates engineered at antibody constant domains can be used for site-specific conjugation of drugs and chelates," *J. Immunological Methods*, 213:131-144 (1998).
Rodwell et al., "Site-specific covalent modification of monoclonal antibodies: In vitro and in vivo evaluations," *PNAS*, 83:2632-2636 (Apr. 1986).
Saito et al., "Drug delivery strategy utilizing conjugation via reversible disulfide linkages: role and site of cellular reducing activities," *Advanced Drug Delivery Reviews*, 55:199-215 (2003).
Stimmel et al., "Site-specific Conjugation on Serine—> Cysteine Variant Monoclonal Antibodies," *J. Biol. Chem.*, 275(39):30445-30450 (2000).
Sun et al., "Reduction-Alkylation Strategies for the Modification of Specific Monoclonal Antibody Disulfides," *Bioconjugate Chem.*, 16:1282-1290 (2005).
Written Opinion of Aug. 17, 2006 for International Application PCT/US05/07239.

* cited by examiner

*Primary Examiner* — Phuong Huynh
(74) *Attorney, Agent, or Firm* — Townsend and Townsend and Crew LLP

(57) ABSTRACT

A protein containing one or more activatable groups, e.g., an antibody, is subjected to partial or complete reduction of one or more such bonds to form reactive groups; the resulting protein is reacted with a drug which is reactive with some of the reactive groups, such as certain radiometals, chelating agents, and toxins, so as to form a conjugate useful in, e.g., in vitro diagnosis, in vivo imaging, and therapy.

26 Claims, 11 Drawing Sheets

*Internal control peaks.

US 7,837,980 B2

PARTIALLY LOADED ANTIBODIES AND METHODS OF THEIR CONJUGATION

This application is the U.S. National Stage of International Application No. PCT/US2005/007239 filed Mar. 2, 2005, which claims the benefit of U.S. Provisional Application No. 60/549,476 filed Mar. 2, 2004; the disclosures, each of which is incorporated by reference herein in its entirety.

BACKGROUND

The present invention is directed to modified proteins having at least one point of conjugation with, for example, a drug resulting in specific isomers of the protein-drug conjugate, and to methods for such conjugation resulting in the specific isomers. The invention is further directed to antibodies to which cytotoxic agents and/or cytostatic agents can be conjugated resulting in specific isomers and methods for their conjugation.

Monoclonal antibodies (mAbs) are a valuable weapon in the battle against cancer. mAbs are also used in the treatment of immune disorders. To further advance the use of mAb-based therapies for cancer and immune disorders, a number of novel approaches have been explored. One approach is to increase the cytotoxic potential of mAbs against tumor cells by attaching cell-killing payloads. Molecules such as protein toxins, radionuclides, and anti-cancer drugs have been conjugated to certain mAbs to generate immunotoxins, radioimmunoconjugates, and antibody-drug conjugates (ADCs), respectively.

Factors which have previously been considered in developing ADCs have included the choice of antibody, and optimizing the potency of the drug component, the stability of the linker, and the method by which the drug was covalently attached to the mAb. The common convention for producing ADCs conjugated through the disulfide bonds has been by reducing all inter-chain disulfide bonds of an antibody and reacting all the reduced nab thiols with a compound capable of interaction with all the reduced thiols, forming uniformly-substituted ADCs with 8 drugs/mAb, i.e. "fully loaded," without the ability to obtain specificity for certain site of conjugation.

For example, the antigen CD30 is highly expressed on cancers such as Hodgkin's disease (HD) and anaplastic large cell lymphomas (ALCL). This expression of CD30, coupled with limited expression on normal cells, makes it an attractive target for ADC therapy. The chimeric mAb directed to CD30, cAC10, has antitumor activity against HD both in vitro and in subcutaneous and disseminated SCID mouse xenograft models. The anti-tumor activity of cAC10 was enhanced by generating fully loaded ADCs in which all eight of the interchain thiols were linked to derivatives of the cytotoxic agent auristatin E as the drug component. These ADCs were highly effective in murine xenograft models at well-tolerated doses.

Because the convention in the production of ADCs has been to fully load them with drug, it was not previously appreciated that partially-loaded ADCs could have the same or greater therapeutic efficacy. Further, methods did not exist which could take into consideration that other substitution patterns on antibodies could produce equal or better therapeutic efficacy with equal or lower toxicity. These and other limitations and problems of the past are solved by the present invention.

BRIEF SUMMARY

The present invention provides protein-drug conjugates and methods of making protein-drug and protein-labeled conjugates. Also provided are proteins having points of conjugation for receiving a drug or label. The conjugates can be used therapeutically, diagnostically (e.g., in vitro or in vivo), for in vivo imaging, and for other uses.

Generally, partially loaded, modified protein having assignable conjugation points are provided. The modified proteins generally include a binding region for interaction with a binding partner and at least two points of conjugation, each point of conjugation covalently linked a drug or label. Typically, less that all possible points of conjugation having a similar accessibility or activability are linked to a drug or label. The modified protein can be, for example, an antibody, a receptor, a receptor ligand, a hormone, a cytokine, or the like. The points of conjugation can be, for example, amino groups, vicinal hydroxyl groups, hydroxyl groups, carboxyl groups, or thiol groups. The protein can be, for example, a receptor, a receptor ligand, a hormone, a cytokine, or the like.

In further embodiments, a method of preparing a conjugate of a protein having one or more disulfide bonds, and a drug reactive with free thiols is provided. The method generally includes partially reducing the protein with a reducing agent; and conjugating the drug reactive with free thiols to the partially reduced protein. In yet another embodiment, a method of preparing a conjugate of a protein having one or more disulfide bonds, and a drug reactive with free thiols, is provided. The method generally includes fully reducing the protein with a reducing agent; partially reoxidizing the protein with a reoxidizing agent; and conjugating the drug reactive with free thiols to the antibody.

In some embodiments, a partially-loaded antibody is provided. The antibody includes an antigen binding region, at least one interchain disulfide bond, and at least two drugs or labels, each drug or label conjugated to an interchain thiol. The points of the conjugation of the drug or label optionally are readily assignable. In an example, the antibody can have at least four cytotoxic or cytostatic drugs, each drug conjugated to an interchain thiol. In certain embodiments, the antibody has the configuration of species 4A, 4B, 4C, 4D, 4E or 4F.

The partially-loaded antibody can be, for example, a murine, humanized, human or chimeric antibody. The drug can be, for example, a cytotoxic or cytostatic agent such as, for example, MMAF, MMAE or AFP. Also provided are pharmaceutical compositions comprising partially loaded antibodies.

In another embodiment, antibodies are provided having at least one point of conjugation for a cytotoxic or cytostatic agent, wherein the point of conjugation for the cytotoxic or cytostatic agent on the antibody can be readily assigned. On the antibody, less than all possible points are conjugation are available for conjugation to the cytotoxic or cytostatic agent. The points of conjugation can be, for example, interchain thiols. The points of conjugation can be, for example, at least one of species 4A through 4F.

A composition of modified antibodies having assignable conjugation points is also provided. The composition can have, for example, at least two, at least four, at least 6 at least 7, at least 10 or more species of modified antibody. In one example, each species can have at least one specified conjugation pairs having two interchain thiols, and at least one interchain disulfide bond. The antibody species can have, for example, 4A, 4B, 4C, 4D, 4E and/or 4F. In further examples, the specified conjugation pair can be at a constant light-constant heavy interchain disulfide bond and/or at a constant heavy-constant heavy interchain disulfide bond. The specified conjugation pair can be proximal to the N-terminal end of the hinge region and/or proximal to the C-terminal end of the hinge region. In another example, the specified conjugation pair is at the constant light-constant heavy interchain sulfide bond and at the hinge region located closer to the N-terminal end of the modified antibody, or at the constant light-constant heavy interchain disulfide bond and at the hinge region located closer to the C-terminal end of the modified antibody.

Each species of antibody optionally can include at least two specified conjugation pairs at the constant light-constant heavy interchain disulfide bonds or at least two specified conjugation pairs at the hinge region interchain disulfide bonds. The composition optionally can further include a pharmaceutically acceptable carrier.

In yet another embodiment, a partially loaded antibody is provided. The antibody includes at least one antigen-binding domain, at least two reactive group on the antibody, and at least two drugs or labels, each drug or label conjugated to a reactive group to form a point of conjugation. The points of conjugation for the drug or label are readily assignable.

In yet other embodiments, a method of reducing and conjugating a drug to an antibody resulting in selectivity in the placement of the drug is provided. The method generally includes fully reducing the antibody with a reducing agent, treating the fully reduced antibody with limiting amounts of a reoxidizing agent to reform at least one interchain disulfide bond of the antibody, such that at least two interchain thiols remain; and conjugating the drug to the interchain thiols. The reoxidizing agent can be, for example, 5,5'-dithio-bis-2-nitrobenzoic acid, 4,4'-dithiodipyridine, 2,2'-dithiodipyridine, sodium tetrathionate or iodosobenzoic acid. The drug can be, for example, a cytotoxic or cytostatic agent or an immunosuppressive agent. In some examples, the drug can be a minor grove binder, AEB, AEVB, MMAF, MMAE or AFP. The reducing agent can be, for example, DTT or TCEP.

In related embodiments, a method of reducing antibody interchain disulfide bonds and conjugating a drug to the resulting interchain thiols resulting in selectivity in the placement of the drugs on the antibody is provided. The method generally includes fully reducing the antibody with a reducing agent to form interchain thiols; partially reoxidizing the antibody with a reoxidizing agent to reform at least one interchain disulfide bond; and conjugating the drug to the interchain thiols. The reoxidizing agent can be, for example, 5,5'-dithio-bis-2-nitrobenzoic acid, 4,4'-dithiodipyridine, 2,2'-dithiodipyridine, sodium tetrathionate, or iodosobenzoic acid. The reducing agent can be, for example, DTT or TCEP. The drug can be, for example, MMAF, MMAE, or AFP. The partially reoxidized antibody optionally can be purified prior to conjugation.

In yet other related embodiments, a method of reducing antibody interchain disulfide bonds and conjugating a drug to the resulting interchain thiols to selectively locate drugs on the antibody is provided. The method generally includes partially reducing the antibody with a reducing agent to form at least two interchain thiols; and conjugating the drug to the interchain thiols of the partially reduced antibody. In an example, the antibody is partially reduced with a limiting concentration of a reducing agent in a buffer with a chelating agent. The drug can be conjugated, for example, by cooling the antibody solution and dissolving the drug in a cold solvent and mixing with the antibody solution. The antibody and drug solution are incubated for a period of time sufficient to form a partially loaded antibody-drug conjugate(s). The reaction can be quenched with a quenching the excess drug with a thiol-containing reagent. The conjugate can be further purified. In a specific example, the antibody is partially reduced for about 1 hour at about 37° C. The reduced antibody can be cooled, for example, to about 0° C. The antibody and drug solution can be incubated, for example, for about 30 minutes at about 0° C.

The thiol-containing reagent can be, for example, cysteine or N-acetyl cysteine. The reducing agent can be, for example, DTT or TCEP. The buffer can be, for example, a sodium borate solution and the chelating agent is dethylenetriaminepentaacetic acid. The chelating agent also can be, for example, ethylenetriaminepentaacetic acid or EDTA. The solvent can be, for example, acetonitrile, alcohol or DMSO. The drug can be, for example, a cytotoxic or a cytostatic agent.

In some embodiments, the reduced antibody can be purified prior to conjugation, using for example, column chromatography, dialysis, or diafiltration. The column used in column chromatography can be, for example, a desalting column, such as a PD-10 column. Alternatively, the reduced antibody is not purified after partial reduction and prior to conjugation.

The conjugate can be purified using, for example, column chromatography, dialysis, or diafiltration. The column used in column chromatography can be, for example, a desalting column, such as a PD-10 column.

In yet another embodiment, a method of producing an antibody with selective conjugation of drug is provided. The method generally includes fully reducing the antibody for a period of time sufficient to produce interchain thiols, as determined by, for example, DTNB titration, by adding a large excess of a reducing agent and incubating the solution at about 37° C. for about 30 minutes; purifying the antibody; partially reoxidizing the antibody using an oxidizing agent to form at least one interchain disulfide bond by cooling the reduced antibody to 0° C.; treating the reduced and cooled antibody with 1.5 to 2.5 molar equivalents of the oxidizing agent; mixing the solution by inversion; allowing the solution to incubate at about 0° C. for about 10 minutes; purifying the partially reoxidized antibody; conjugating the drug to the interchain thiols of the partially reoxidized antibody to form a conjugated antibody; and purifying the conjugated antibody.

The reducing agent can be, for example, DTT or TCEP. The partially-reduced antibody optionally can be purified, for example, using column chromatography, dialysis, or diafiltration. The column used in column chromatography can be, for example, a desalting column such as a PD-10 column. The conjugated antibody can be purified, for example, using column chromatography, dialysis, or diafiltration. The column used in column chromatography can be, for example, a desalting column such as a PD-10 column. The reoxidizing agent can be, for example, 5,5'-dithio-bis-2-nitrobenzoic acid, 4,4'-dithiodipyridine, 2,2'-dithiodipyridine, sodium tetrathionate, or iodosobenzoic acid.

The invention will best be understood by reference to the following detailed description of the specific embodiments, taken in conjunction with the accompanying drawings. The discussion below is descriptive, illustrative and exemplary and is not to be taken as limiting the scope defined by any appended claims.

BRIEF DESCRIPTION OF SEVERAL VIEWS OF THE DRAWINGS

(Referring to FIG. 1, note that species 4A is a mirror image of species 4C and species 4B is a mirror image of species 4D. In FIG. 7, species 4A and 4C are referred to as 4A, and species 4B and 4D are referred to as 4B.) The interchain disulfide bonds are shown as solid lines between the heavy-heavy chains or the heavy-light chains of the antibody. The drugs and their point of conjugation to the antibody are shown as circles.

FIG. 12A shows the results with SCID mice bearing Karpas-299 subcutaneous tumors injected with cAC10-E2 at 0.5 mg/kg or 1.0 mg/kg every four days for four injections. cAC10-E4 and cAC10-8 were dosed at either 0.25 or 0.5 mg/kg every four days for four injections. FIG. 12B shows the results with SCID mice with Karpas-299 subcutaneous tumors were treated with a single dose of E2, E4 or E8 at 1.0 mg/kg.

DETAILED DESCRIPTION

Figure 1:
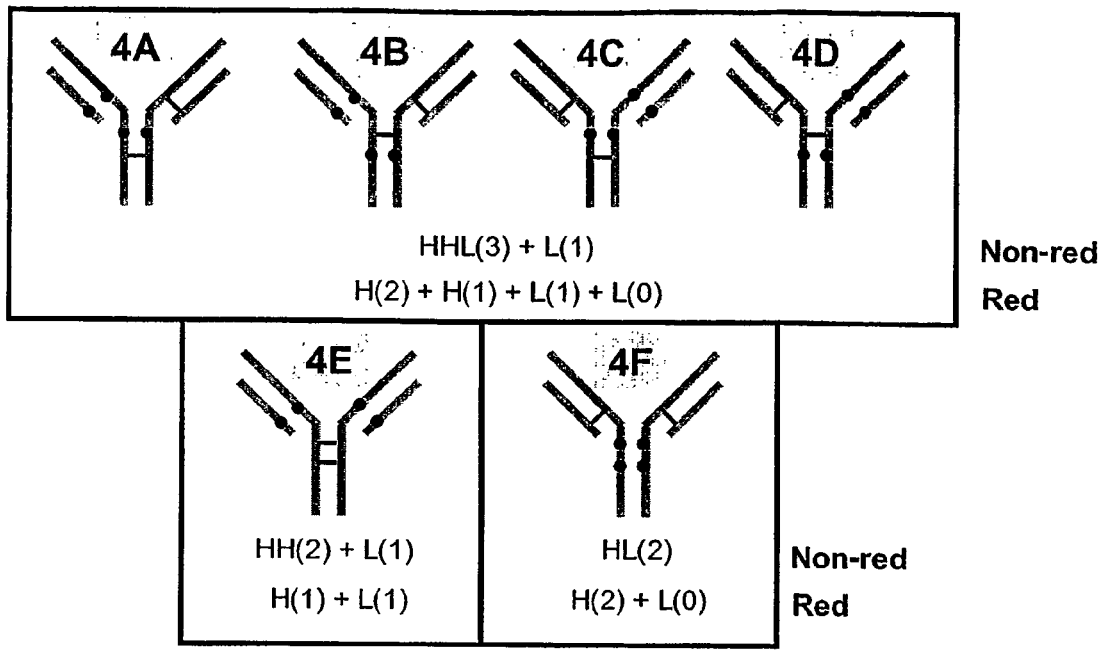
FIG. 1 shows the "E4" isomers (isomers with four drugs attached per antibody) of a cartoon antibody. The interchain disulfide bonds are shown as solid lines between the heavy-heavy chains of the antibody or the heavy-light chains of the antibody. The drugs and their points of conjugation to the antibody are shown as circles. The fragments generated under non-reducing ("Non-red") and reducing ("Red") conditions are shown below each isomer (with the number of drugs per fragment in parentheses).

For clarity of disclosure, and not by way of limitation, the detailed description of the invention is divided into the subsections which follow.

I. Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "drug" as used herein means an element, compound, agent, or molecular entity, including, e.g., a pharmaceutical, therapeutic, or pharmacologic compound. Drugs can be natural or synthetic or a combination thereof. A "therapeutic drug" is an agent that exerts a therapeutic (e.g., beneficial) effect on cancer cells or immune cells (e.g., activated immune cells), either alone or in combination with another agent (e.g., a prodrug converting enzyme in combination with a prodrug). Typically, therapeutic drugs useful in accordance with the methods and compositions described herein are those that exert a cytotoxic, cytostatic, or immunosuppressive effect. In certain embodiments, a drug is not a radioactive element.

"Cytotoxic agent," in reference to the effect of an agent on a cell, means killing of the cell.

"Cytostatic agent" means an inhibition of cell proliferation.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more CDRs). The term "fragment" refers to a portion of a polypeptide typically having at least 20 contiguous or at least 50 contiguous amino acids of the polypeptide. A "derivative" includes a polypeptide or fragment thereof having conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included are, for example, polypeptide analogs containing one or more analogs of an amino acid (e.g., unnatural amino acids and the like), polypeptides with unsubstituted linkages, as well as other modifications known in the art, both naturally and non-naturally occurring. Polypeptide analogs include, for example, protein mimetics and bombesin.

The term "antibody" as used herein refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen, or (b) conservatively substituted derivatives of such immunoglobulin polypeptides or fragments that immunospecifically bind to the antigen. Antibodies are generally described in, for example, Harlow & Lane, Antibodies: A Laboratory Manual (Cold Spring Harbor Laboratory Press, 1988).

An "antibody derivative" as used herein means an antibody, as defined above, that is modified by covalent attachment of a heterologous molecule such as, e.g., by attachment of a heterologous polypeptide, or by glycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

The term "interchain disulfide bond," in the context of an antibody, refers to a disulfide bond between two heavy chains, or a heavy and a light chain.

The term "interchain thiol" refers to a thiol group of an antibody heavy or light chain that can participate in the formation of an interchain disulfide bond.

A protein is referred to as "fully-loaded" when all points of conjugation of a particular type and/or of similar reactivity are conjugated to drugs, resulting in a homogeneous population of protein-drug conjugate. A protein is referred to as "partially-loaded" when only some of the possible points of conjugation of a particular type and/or of a similar reactivity are conjugated to drugs, resulting in formation of a certain isomer or isomers of the protein-drug conjugate.

The term "isolated," in the context of a molecule or macromolecule (e.g., an antibody) is one which has been identified and separated and/or recovered from a component of its natural environment. Contaminant components of its natural environment are materials which would interfere with the desired use (e.g., diagnostic or therapeutic) of the molecule, and may include enzymes, hormones, and other proteinaceous or nonproteinaceous solutes. In some embodiments, an isolated molecule or macromolecule will be purified (1) to greater than 95%, or greater than 99%, by weight of the molecule or macromolecule as determined by, for example, the Lowry or Bradford methods, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated molecules and macromolecules include the molecule and macromolecule in situ within recombinant cells since at least one component of the antibody's natural environment will not be present. Ordinarily, however, isolated antibody will be prepared by at least one purification step.

The abbreviation "AFP" refers to dimethylvaline-valine-dolaisoleuine-dolaproine-phenylalanine-p-phenylenediamine having the general formula shown immediately following:

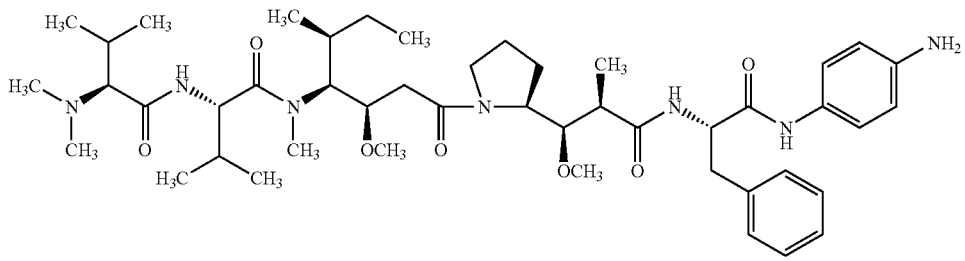

The abbreviation "MMAE" refers to monomethyl auristatin E having the general formula shown immediately following:

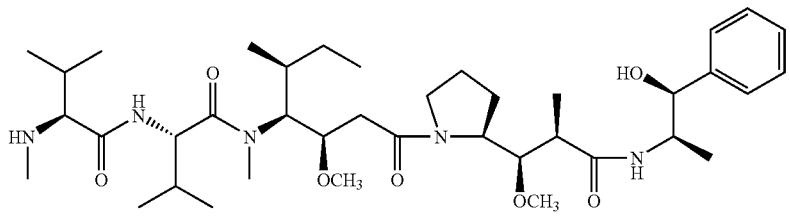

The abbreviation "MMAF" refers to dovaline-valine-dolaisoleuine-dolaproine-phenylalanine having the general formula shown immediately following:

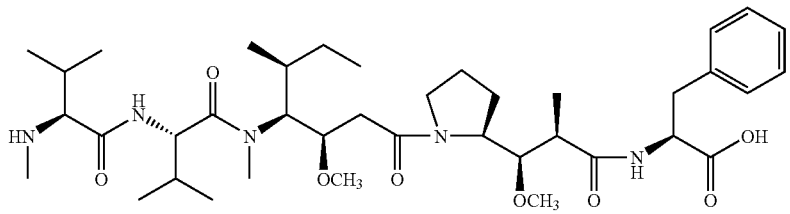

The abbreviation "AEB" refers to an ester produced by reacting auristatin E with paraacetyl benzoic acid. The abbreviation "AEVB" refers to an ester produced by reacting auristatin E with benzoylvaleric acid.

The phrase "pharmaceutically acceptable salt," as used herein, refers to pharmaceutically acceptable organic or inorganic salts of a molecule or macromolecule. Acid addition salts can be formed with amino groups. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, melthanesulfonate, ethanesulfonate, benzenesulfonate, p-toluenesulfonate, and pamoate (i.e., 1,1' methylene bis-(2-hydroxy 3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a molecule or macromolecule. Examples of solvents that form pharmaceutically acceptable solvates include, but are not limited to, water, isopropanol, ethanol, methanol, DMSO, ethyl acetate, acetic acid, and ethanolamine.

II. Polypeptides, Proteins, Antibodies

The present invention provides protein-drug conjugates and methods of making protein-drug conjugates. Also provided are proteins having points of conjugation for receiving a drug. The protein-drug conjugates can be used therapeutically, diagnostically (e.g., in vitro or in vivo), for in vivo imaging, and for other uses.

Various classes of proteins can be conjugated, including antibodies, enzymes, glycosylated proteins, lectins, various biological receptors, protein hormones, and other proteins that can serve as a binding agent for a binding partner. The proteins contain at least one reactive site, such as a disulfide bond, amino group, hydroxyl group or carboxyl group, where conjugation of a drug to the protein can occur.

The reactive site is accessible and capable of activation, such as by chemical or means. In some embodiments, the protein to be chemically activated for conjugation purposes is one containing disulfide bonds non-essential for the intended use of the protein, and/or one which would not interfere with the protein (such as but not limited to causing degradation of the protein or interfere with binding or other functions (e.g., effector function.)). In such a protein, a disulfide bond is present as a result of the oxidation of the thiol (—SH) side groups of two cysteine residues. These residues may lie on different polypeptide chains, or on the same polypeptide chain. As a result of the oxidation, a disulfide bond (—S—S—) is formed between the beta carbons of the original cysteine residues. After reduction, the residues are termed often interchangeably half-cystines and cystine. Treatment of the disulfide bond with a reducing agent causes reductive cleavage of the disulfide bonds to leave free thiol groups. Examples of proteins containing disulfide bonds include antibodies, many enzymes, certain hormones, and certain receptors.

In some embodiments, the disulfide bond can be naturally occurring. In some embodiments, a sulfhydryl group(s) can also be chemically introduced into a protein (e.g., an antibody). Suitable methods for introducing sulfhydryl groups include chemical means (e.g., using a thiolating agent such as 2-IT), or using recombinant DNA technology. For example, cysteine residues can be introduced into a protein by mutagenesis of a nucleic acid encoding the protein. See generally Sambrook et al., Molecular Cloning, A Laboratory Manual, 3rd ed., Cold Spring Harbor Publish., Cold Spring Harbor, N.Y. (2001); Ausubel et al., Current Protocols in Molecular Biology, 4th ed., John Wiley and Sons, New York (1999); which are incorporated by reference herein.) Sulfhydryl groups can be introduced into a protein, for example, within the polypeptide or at the carboxy-terminus.

In some embodiments, the protein is an antibody. Such an antibody may be used in in vitro or in vivo diagnosis, in vivo imaging, or therapy of diseases or conditions with distinctive antigens. The basic unit of an antibody structure is a complex of four polypeptides—two identical low molecular weight ("light") chains and two identical high molecular weight ("heavy") chains, linked together by both non-covalent associations and by disulfide bonds. Different antibodies will have anywhere from one to five of these basic units. The antibody may be represented schematically as a "Y". Each branch of the "Y" is formed by the amino terminal portion of a heavy chain and an associated light chain. The base of the "Y" is formed by the carboxy terminal portions of the two heavy chains. The node of the "Y" is referred to as the hinge region.

Five human antibody classes (IgG, IgA, IgM, IgD and IgE), and within these classes, various subclasses (e.g., IgG1, IgG2, IgG3, IgG4, IgA1 and IgA2) or subclass of immunoglobulin molecule, are recognized on the basis of structural differences, such as the number of immunoglobulin units in a single antibody molecule, the disulfide bridge structure of the individual units, and differences in chain length and sequence. The class and subclass of an antibody is its isotype.

The antibody can be an intact antibody or an antigen-binding antibody fragment such as, for example, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, or fragments produced by a Fab expression library. Antigen-binding antibody fragments, including single-chain antibodies, can comprise the variable region(s) alone or in combination with the entirety or a portion of the following: hinge region, $C_H1$, $C_H2$, $C_H3$, $C_H4$ and $C_L$ domains. Also, antigen-binding fragments can comprise any combination of variable region(s) with a hinge region, $C_H1$, $C_H2$, $C_H3$, $C_H4$ and $C_L$ domains. In some embodiments, an antibody fragment comprises at least one domain, or part of a domain, that includes interchain disulfide bonds.

Typically, the antibodies are human, rodent (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. Nos. 5,939,598 and 6,111,166. The antibodies may be monospecific, bispecific, trispecific, or of greater multispecificity.

In some embodiments, the constant domains have effector function. The term "antibody effector function(s)," or AEC, as used herein refers to a function contributed by an Fc domain(s) of an Ig. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the CD70 targeted cell. The effector function can be, for example, "antibody-dependent cellular cytotoxicity" or ADCC, "antibody-dependent cellular phagocytosis" or ADCP, "complement-dependent cytotoxicity" or CDC. In other embodiments, the constant domain lack one or more effector functions.

The antibodies may be directed against antigen of interest, such as medical and/or therapeutic interest. For example, the antigen can be one associated with pathogens (such as but not limited to viruses, bacteria, fungi, and protozoa), parasites, tumor cells, or particular medical conditions. In the case of a tumor-associated antigen (TAA), the cancer may be of the immune system, lung, colon, rectum, breast, ovary, prostate gland, head, neck, bone, or any other anatomical location. Antigens of interest include, but are not limited to, CD30, CD40, Lewis Y, and CD70. In some embodiments, the antigen is CD2, CD20, CD22, CD33, CD38, CD40, CD52, HER2, EGFR, VEGF, CEA, HLA-DR, HLA-Dr10, CA125, CA15-3, CA19-9, L6, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, gp100, MART1, IL-2 receptor, human chorionic gonadotropin, mucin, P21, MPG, and Neu oncogene product.

Some specific useful antibodies include, but are not limited to, BR96 mAb (Trail et al. (1993), Science 261:212-215), BR64 (Trail et al. (1997), Cancer Research 57:100-105), mAbs against the CD 40 antigen, such as S2C6 mAb (Francisco et al. (2000) Cancer Res. 60:3225-3231), and mAbs against the CD30 antigen, such as AC 10 (Bowen et al. (1993) J. Immunol. 151:5896-5906). Many other internalizing antibodies that bind to tumor specific antigens can be used, and have been reviewed (see, e.g., Franke et al. (2000), Cancer Biother Radiopharm. 15:459-76; Murray (2000), Semin Oncol. 27:64-70; Breitling et al., Recombinant Antibodies, John Wiley, and Sons, New York, 1998). The disclosures of these references are incorporated by reference herein.

The term "tumor-specific antigen" as used herein will be understood to connote an antigen characteristic of a particular tumor, or strongly correlated with such a tumor. However, tumor-specific antigens are not necessarily unique to tumor tissue, however, i.e., that antibodies to them may cross-react with antigens of normal tissue. Where a tumor-specific antigen is not unique to tumor cells, it frequently occurs that, as a practical matter, antibodies binding to tumor-specific antigens are sufficiently specific to tumor cells to carry out the desired procedures without unwarranted risk or interference due to cross-reactions. Many factors contribute to this practical specificity. For example, the amount of antigen on the tumor cell may greatly exceed the amount of the cross-reactive antigen found on normal cells, or the antigen on the tumor cells may be more effectively presented. Therefore the term "tumor-specific antigen" relates herein to a specificity of practical utility, and is not intended to denote absolute specificity or to imply an antigen is unique to the tumor.

The antibody may be a polyclonal antibody or a monoclonal antibody. When the subject is a human subject, the antibody may be obtained by immunizing any animal capable of mounting a usable immune response to the antigen. The animal may be a mouse, rat, goat, sheep, rabbit or other suitable experimental animal. The antigen may be presented in the form of a naturally occurring immunogen, or a synthetic immunogenic conjugate of a hapten and an immunogenic carrier. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Human monoclonal antibodies may be made by any of numerous techniques known in the art (e.g., Teng et al. (1983), Proc. Natl. Acad. Sci. USA. 80, 7308-7312; Kozbor et al. (1983) Immunology Today 4, 72-79; and Olsson et al. (1982), Meth. Enzymol. 92, 3-16).

The antibody can be, for example, a murine, a chimeric, humanized, or fully human antibody produced by techniques well-known to one of skill in the art. Recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 184,187; European Patent Publication No. 171496; European Patent Publication No. 173494; International Publication No. WO 86/01533; European Patent Publication No. 12,023; Berter et al. (1988), Science 240:1041-1043; Liu et al. (1987), Proc. Natl. Acad. Sci. USA 84:3439-3443; Liu et al. (1987), J. Immunol. 139:3521-3526; Sun et al. (1987), Proc. Natl. Acad. Sci. USA 84:214-218; Nishimura et al. (1987), Cancer. Res. 47:999-1005; Wood et al. (1985), Nature 314:446-449; and Shaw et al. (1988), J. Natl. Cancer Inst. 80:1553-1559; Morrison (1985), Science 229:1202-1207; Oi et al. (1986), BioTechniques 4:214; U.S. Pat. No. 5,225,539; Jones et al. (1986), Nature 321:552-525; Verhoeyan et al. (1988), Science 239:1534; and Beidler et al. (1988), J. Immunol. 141: 4053-4060; each of which is incorporated herein by reference in its entirety.

Completely human antibodies can be produced, for example, using transgenic mice that are incapable of expressing endogenous immunoglobulin heavy and light chains genes, but which can express human heavy and light chain genes. The transgenic mice are immunized in the normal fashion with a selected antigen or a portion thereof. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. See, e.g., Jespers et al. (1994), Biotechnology 12:899-903. Human antibodies can also be produced using various techniques known in the art, including phage display libraries (Hoogenboom and Winter (1991), J. Mol. Biol. 227: 381; Marks et al. (1991), J. Mol. Biol. 222:581; Quan and Carter (2002), "The rise of monoclonal antibodies as therapeutics." In Anti-IgE and Allergic Disease, Jardieu, P. M. and Fick Jr., R. B, eds., Marcel Dekker, New York, N.Y., Chapter 20, pp. 427-469.

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al. (1991), EMBO J. 10:3655-3659.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al. (1986), Methods in Enzymology 121:210; Rodrigues et al. (1993), J. Immunology 151:6954-6961; Carter et al. (1992), Bio/Technology 10:163-167; Carter et al. (1995), J. of Hematotherapy 4:463-470; Merchant et al. (1998), Nature Biotechnology 16:677-681. Using such techniques, bispecific antibodies can be prepared for use in the treatment or prevention of disease.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not the antibody. Preferably, the antibody or fragment thereof is covalently linked to the other protein at the N-terminus of the constant domain.

In yet other embodiments, the protein can be a fusion protein of the binding portion of a non-antibody molecule fused via a covalent bond to the antibody heavy and/or light chain constant region domain, optionally including a hinge region. Such a fusion protein optionally can include at least one, typically at least two, interchain disulfide bonds. For example, the fusion protein can include the $C_H1$ and $C_L$ regions, and a hinge region.

III. Activation Methods

In general, a drug can be coupled to a protein or other suitable molecule at an activatable site. Suitable activatable sites include conjugation points such as thiol groups, amino groups (e.g., the epsilon amino group of lysine residues or at the N-terminus of proteins), vicinal hydroxyl groups (1,2-diols) (e.g., oxidized carbohydrates) and carboxyl groups (e.g., the C-terminus of proteins, aspartic acid and glutamic acid residues, and carbohydrate, such as sialic acid residues).

A drug can be coupled directly to a conjugation point. For example, a drug can be attached by alkylation of the ε-amino group of antibody lysines, reductive amination of oxidized carbohydrate or reaction with a hydrazide, transesterification between hydroxyl and carboxyl groups, amidation at amino groups or carboxyl groups, and conjugation to thiols (e.g., interchain thiols) or introduced thiols by, for example, alkylating lysines with 2-iminothiolane (Traut's reagent). Suitable methods conjugating drugs to conjugation points are disclosed in, for example, Current Protocols in Protein Science (John Wiley & Sons, Inc.), Chapter 15 (Chemical Modifications of Proteins) (the disclosure of which is incorporated by reference herein in its entirety.)

A drug also can be coupled indirectly via another molecule, such as a linker. For example, a drug also can be conjugated via a maleimide group coupled to a sulfhydryl group in, for example, but not limited to, the hinge region of an antibody. Antibody conjugates can be made by reacting a maleimide-derivatized form of the drug with the antibody. More specifically, antibody conjugates can be made by reducing an antibody to produce the reduced antibody, producing an amine drug, derivatizing the amine drug with maleimide to produce a maleimide-derivatized drug, and reacting the maleimide-derivatized drug with the antibody.

In an exemplary embodiment, an $IgG_1$ such as cAC10 possesses many disulfide bonds, only four of which are interchain. Because the four interchain disulfide bonds are clustered in the highly-flexible hinge region and much more solvent-accessible than other (intra-chain) disulfide bonds, reduction with an excess of, for example, a reducing agent, such as but not limited to dithiothreitol (DTT), Tris(2-carboxyethyl)phosphine (TCEP), or 2-Mercaptoethanol, breaks all four bonds and generates eight cysteines (i.e., containing the free thiol group). Conjugation of all eight cysteines with the drug-linker generates a fully-loaded conjugate with approximately eight drugs per antibody, as shown in see FIG. 7.

The present invention surprisingly demonstrates that the biological properties of ADCs can be improved with antibodies having an average of 2, 2.5, 4 or 6 drugs per antibody, which yields lower toxicity while maintaining the efficacy of fully loaded conjugates, i.e. conjugates having 8 drugs per antibody. The therapeutic window (concentration of drug-antibody conjugate where toxicity is first seen divided by the lowest efficacious dose) of partially-drug loaded conjugates is larger than antibodies with 8 drugs. There are a number of ways to conjugate the 8 cysteines with 4 drugs, yielding a large number of potential drug loaded species (9 total, with 0 through 8 drugs per antibody, see FIGS. 1 and 7). For those antibodies that have 4 drugs, there are 6 possible ways to distribute the 4 drugs, yielding 6 isomers (See FIGS. 1 and 7). The homogeneity of the 8 drug loaded species is lost when 4 drugs per antibody is desired. For antibodies with 2 or 6 drugs per antibody, there are three possible ways to distribute the drugs on the molecules.

Methods to produce partially loaded ADCs (e.g., with 4 (E4) rather than 8 drugs per antibody) include the following: method 1 ("partial reduction") partial reduction of the antibody by a reducing agent such as but not limited to DTT or TCEP followed by conjugation, and method 2 ("full reduction and reoxidation") full reduction of the antibody with a reducing agent such as but not limited to DTT or TCEP, followed by partial reoxidation of the antibody with a reoxidizing agent (for example but not limited to 5,5'-dithio-bis-2-nitrobenzoic acid (DTNB), 4,4'-dithiodipyridine, 2,2'-dithiodipyridine, sodium tetrathionate, or iodosobenzoic acid) and finally conjugation. In the full reduction and reoxidation method, there are two aspects: 2a purification after DTNB reoxidation, and 2b, no purification after DTNB reoxidation (one pot reoxidation and drug conjugation). These methods yield different percent of different species (e.g., for E4 from 25 to 40%) and also yield different isomeric mixtures of the possible species. Encompassed in the disclosure are hybrids and variations of the above methods which would be known to one of skill in the art.

As an example for antibody drug conjugates, FIG. 1 shows the 6 possible E4 species (referred to as 4A through 4F species) that can be generated during a conjugation reaction. Species 4A-D are not individually distinguishable by certain analytic methods; however, they can be distinguished from both 4E and 4F.

In one embodiment of method 1 of partial reduction, conjugates with, for example, 4 drugs per antibody can be made by full reduction of the antibody with, for example but not limited to DTT, to yield 8 antibody cysteines followed by conjugation to 4 equivalents of drug. This leads to a mixture where antibodies have from 0 to 8 drugs. Alternatively, if the antibody is reduced by limiting quantities of, for example DTT, such that an average of only 2 of the 4 disulfides are reduced (liberating 4 cysteines) followed by complete drug conjugation, only even drug loaded species (0, 2, 4, 6, and 8 drugs per antibody) will be formed. This reduces the complexity of the mixture, which can be further reduced by purification to isolate these different drug loaded species.

In some embodiments, certain potential points of conjugation on a protein can be selectively activated. This selective activation allows for ready assignability of the conjugation site(s) of a drug on the protein. For example, treatment of an antibody (e.g., cAC10) with limiting amounts of the strong reducing agents DTT or TCEP results in the selective reduction of the heavy-light chain disulfides. In another example, full DTT reduction of an antibody followed by partial reoxidation using a strong thiol oxidizing agent such as DTNB results in selective reoxidation of the heavy-light chain hinge disulfides, leading to drug predominantly conjugated on the heavy chain in the hinge region. The isomer populations of E2 and E6 produced by both of these methods can approach 90% isomeric homogeneity.

Following conjugation of the drug to the antibody, the conjugated drug-antibody species can be separated. In some embodiments, the conjugated antibody species can be separated based on the characteristics of the antibody, the drug and/or the conjugate. For example, hydrophobic interaction chromatograph (HIC) has been successful in isolating and separating species corresponding to 0, 2, 4, 6, and 8 drugs per antibody. The yields of each of these drug loaded isomers by method 1 is close to what would be expected by a statistical distribution. The 4 drug loaded species is typically 30% of the total material.

Analytical methods have been developed to determine drug loading and the location of the drugs on the antibody (see also infra). Characterization of the pure 4 drug loaded conjugates prepared by partial DTT reduction by Bioanalyzer (capillary electrophoresis) and HPLC on a crosslinked divinylbenzene column (PLRP) revealed that the drugs are predominantly located on cysteines that originally made disulfides between the heavy and light chains of the antibody. The specificity of the drug location, where one isomer is favored over the other five isomers, unlike the convention, is unexpected.

In another embodiment, method 2, full reduction with partial reoxidation, to prepare drug-antibody conjugates with, for example, 4 drugs, the antibody was fully reduced with, for example but not limited to, DTT and then treated with limiting amounts of, for example but not limited to, DTNB to reform some of the disulfides such that 4 antibody cysteine thiols remained. These cysteines were conjugated to drug and analyzed by the methods described herein. The yield of 4 drug loaded antibodies in the mixture increased to as much as 40%, and once purified the location of the drug favored placement on the cysteines that originally made disulfides between the heavy chains in the hinge region. Both the yield of 4 drug loaded antibodies and the selectivity compared to common convention, which favors a different isomer from certain partial reduction methods, are unexpected. Using various chemical means, drug location within the antibody can be readily assigned for the production of different isomers.

Figure 7:
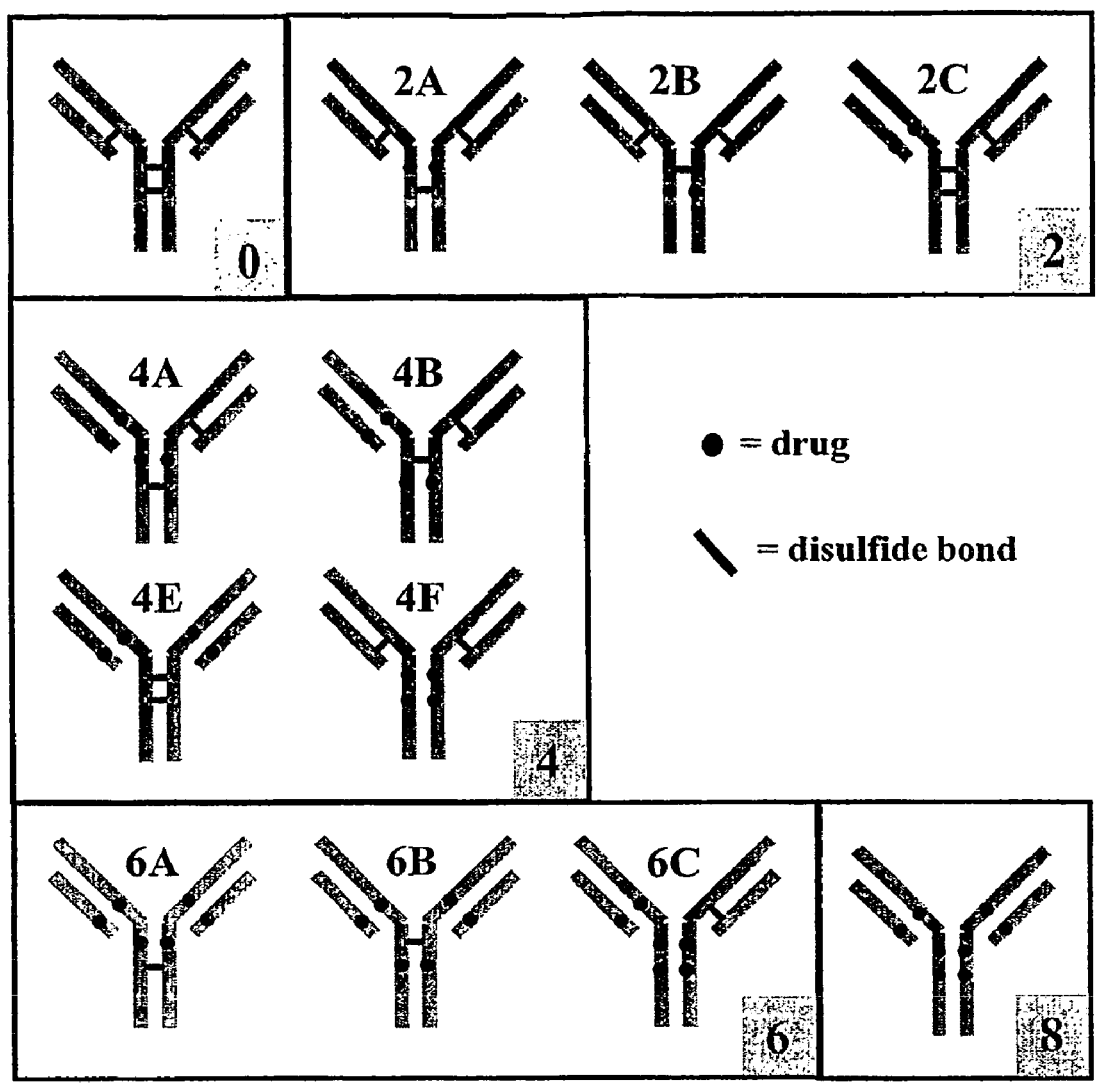
FIG. 7 shows a cartoon representation of the major conjugate species obtained by reduction, full or partial, of the inter-chain disulfide bonds followed by conjugation with a drug. Full reduction and conjugation produces primarily the fully-loaded species with 8 drugs per antibody, whereas partial reduction and conjugation can lead to the generation of all the shown species. There is only one isomer each for the 0 and 8 drug-loaded species, whereas the 2, 4 and 6 drug-loaded species contain 3, 4 and 3 isomers, respectively.

If reduction is controlled by addition of limiting amounts of reducing agent, partial reduction occurs in which, on average, less than four inter-chain disulfide bonds are broken per antibody. Because all four inter-chain disulfide bonds are highly exposed, reduction proceeds through various pathways and produces partially-reduced antibody composed of a mixture of species with 0, 2, 4, 6, or 8 cysteines. Conjugation of partially-reduced antibody, therefore can generate a mixture of conjugates with 0, 2, 4, 6, or 8 drugs per antibody, as shown in FIGS. 1 and 7. Depending on the extent of partial reduction, the drug-load distribution (i.e., the percent of 0, 2, 4, 6, or 8 drug-loaded species) changes.

Partial reduction not only produces a mixture containing species with variable number of drugs per antibody, it also creates further heterogeneity as a result of the multiple locations of drug attachment. FIG. 7 shows that there is more than one isomer possible for the 2, 4, and 6 drug-loaded species.

Following conjugation of the drug to a protein, the conjugated drug-protein species can be separated. For example, in some embodiments, the conjugated antibody species can be separated based on the characteristics of the antibody, the drug and/or the conjugate. For example, hydrophobic interaction chromatograph (HIC) has been successful in isolating and separating species corresponding to 0, 2, 4, 6, and 8 drugs per antibody.

IV. Analytical Methods

Figure 2:
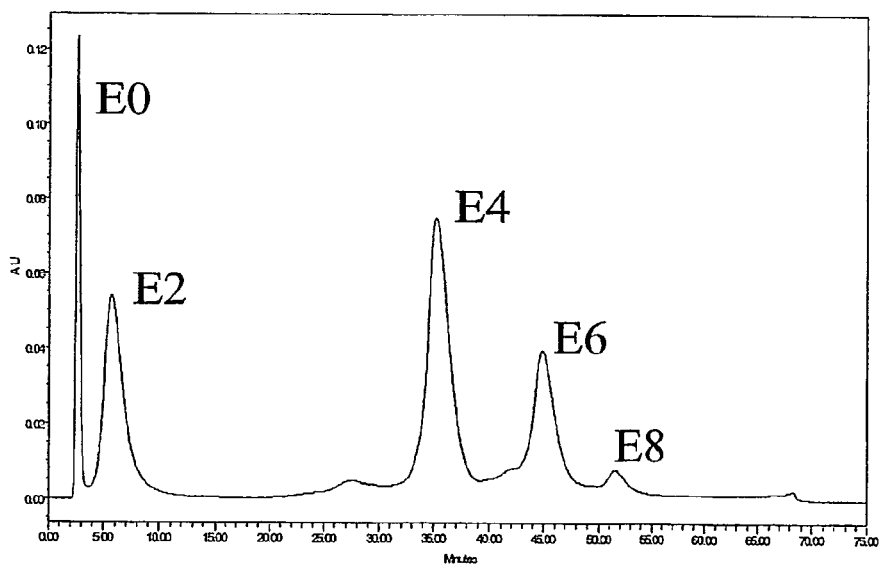
FIG. 2 shows a chromatogram of the elution profile of a hydrophobic interaction chromatography (HIC) analysis of vcMMAE-cAC10 conjugate prepared by one aspect of method 2a: partial DTNB reoxidation, PD-10 purification, and vcMMAE conjugation. "E0", "E2", "E4", "E6" and "E8" refer to the isomers of the cAC10 antibody with 0, 2, 4, 6 and 8 MMAF molecules attached per antibody, respectively.
Figure 3:
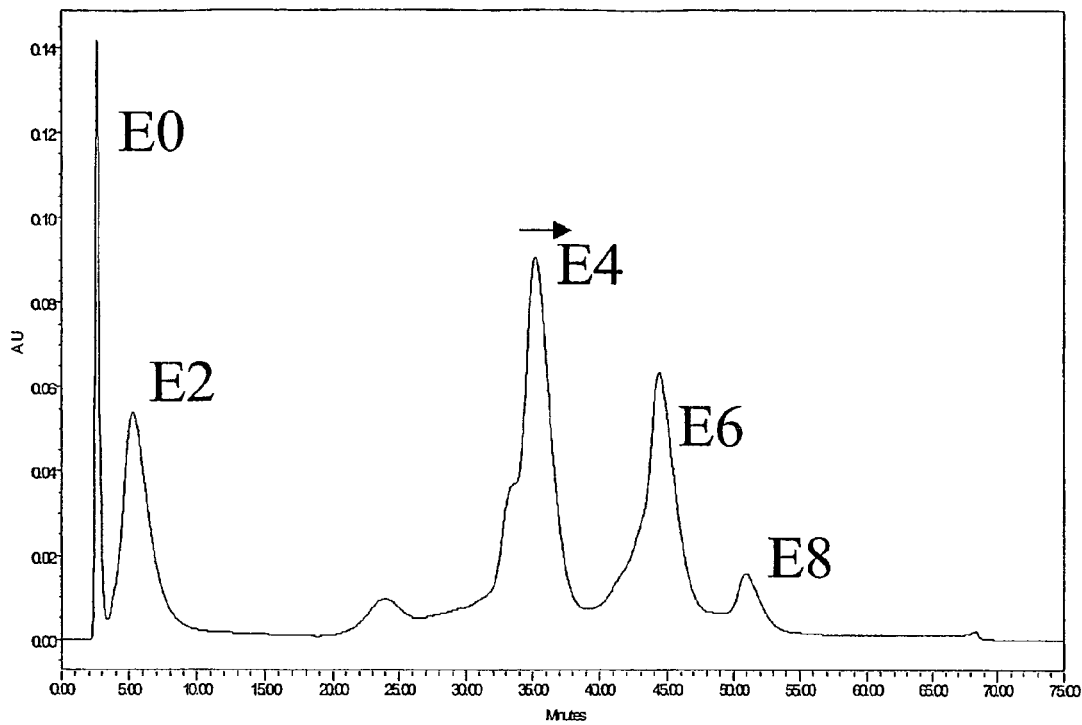
FIG. 3 shows a HIC chromatogram for another aspect of method 2b: one-pot DTNB reoxidation and vcMMAE conjugation. E0", "E2", "E4", "E6" and "E8" refer to the isomers of the cAC10 antibody with 0, 2, 4, 6 and 8 MMAF molecules attached per antibody, respectively. Pure E4 was collected from about 34-38 min (indicated by arrow).
Figure 4:
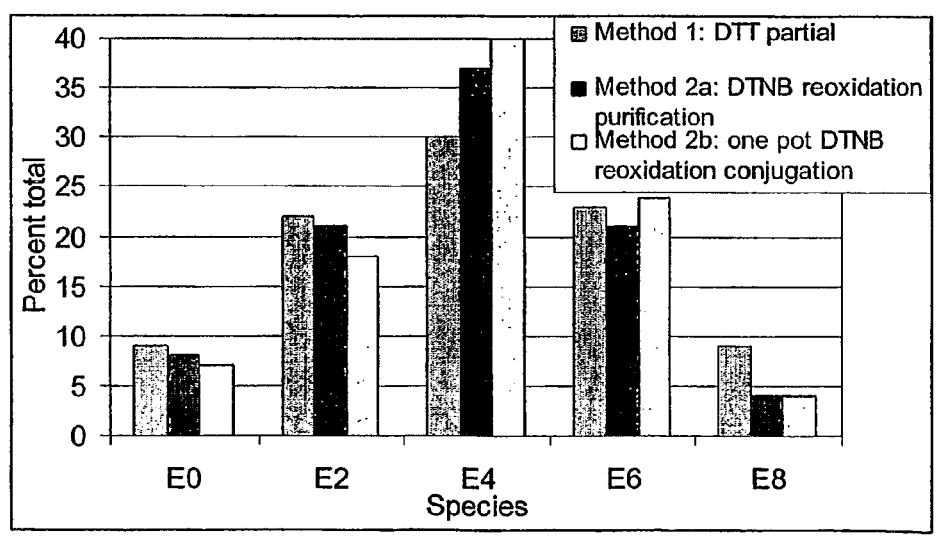
FIG. 4 shows bar graph comparison of the percent composition of antibody-drug conjugates for even drug loaded species from methods 1, 2a, and 2b. For each species, antibody-drug conjugates were prepared by the DTT partial reduction (left bar), DTNB reoxidation (middle bar) or one pot DTNB reoxidation (right bar) conjugation methods.

Various analytical methods can be used to determine the yields and isomeric mixtures of the conjugates. For example, in one embodiment HIC is the analytical method used to determine yields and isomeric mixtures from resultant conjugates (e.g., for E4 conjugates). This technique is able to separate antibodies loaded with various numbers of drugs. The drug loading level can be determined based on the ratio of absorbances, e.g., at 250 nm and 280 nm. For example, if a drug can absorb at 250 nm while the antibody absorbs at 280 nm. The 250/280 ratio therefore increases with drug loading. Using the conjugation methods described herein, generally antibodies with even numbers of drugs were observed to be conjugated to the antibody since reduction of disulfides yields even numbers of free cysteine thiols. FIGS. 2 and 3 show HIC separations for cAC10-vcMMAE produced by methods 2a and 2b, respectively. FIG. 4 shows the percent composition for the various substitutions from these chromatograms as well as from method 1. Method 1 yields about 30% E4, while method 2b yields about 40% E4.

HIC can also be used preparatively at milligram to gram levels to purify E4 from a mixture of substitution levels. Pure E4 from FIG. 3 (collection time of 34-38 min indicated) was obtained and analyzed by two methods to determine the isomeric E4 mixture. First, an Agilent Bioanalyzer was used, which denatures noncovalent interactions and separates based on protein mass, yielding the following antibody components in order of elution: light chain (L), heavy chain (H), heavy-light (HL), heavy-heavy (HH), heavy-heavy-light (HHL), and heavy-heavy-light-light (HHLL). The smaller species are formed when disulfides are reduced and the free thiols conjugated to vcMMAE.

Figure 5:
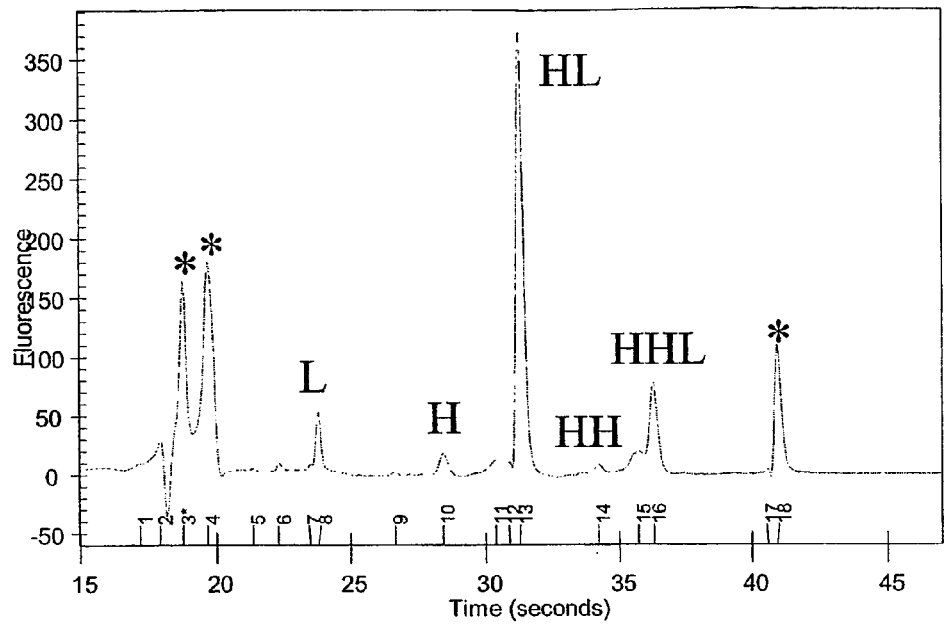
FIG. 5 shows a bioanalyzer trace for E4 material collected as indicated in the HIC chromatogram in FIG. 3 (method 2b). "L" indicates free light chains. "H" indicates free heavy chains. "HL" indicates associated heavy-light chains. "HH" indicates associated heavy-heavy chains. "HHL" indicates associated heavy-heavy and heavy-light chains.

FIG. 1 also describes which antibody components will be observed from denaturation of the various E4 isomers. As can be seen in FIG. 5, pure E4 prepared by method 2b is dominated by HL, with a small amount of L and HHL. This result can be explained by the presence of mostly species 4F (exclusively yields HL) with some species 4A-D (yielding HHL and L). Interestingly, the same analysis of cAC10-vcMMAE made by method 1 yields approximately equal amounts of L, HL, and HH, which would be consistent with a mixture of mostly species 4E and some species 4F.

Figure 6:
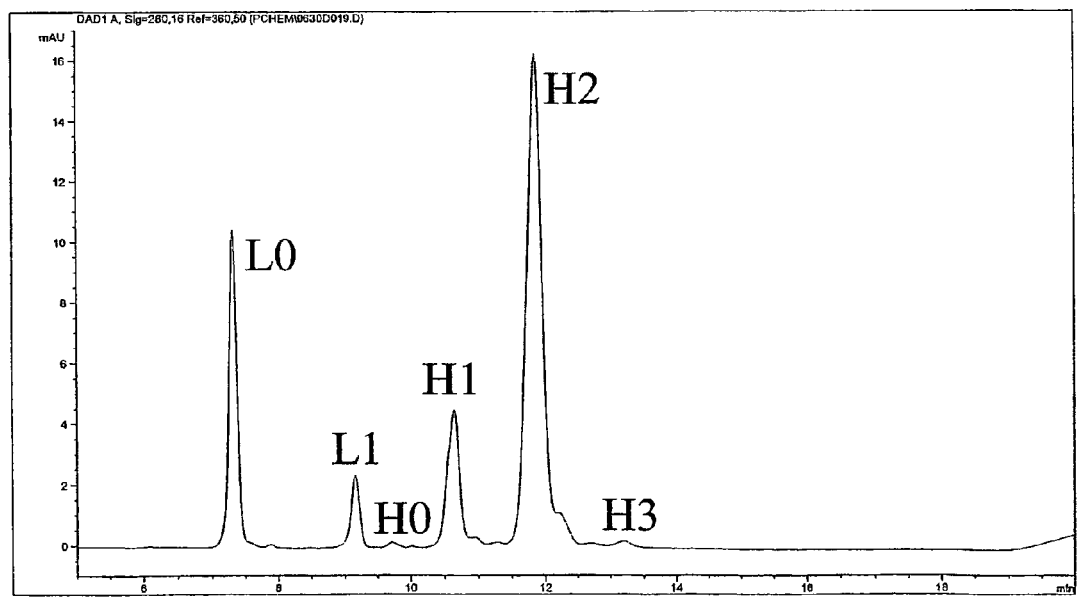
FIG. 6 shows PLRP analysis of material collected from the HIC chromatogram in FIG. 3 (method 2b). "L0" and "L1" indicate a light chain with no or one drug molecule attached, respectively. "H0", "H1", "H2" and "H3" indicate a heavy chain with zero, one, two or three drug molecules attached.

Another embodiment of an analytical tool is chromatography on a reversed-phase PLRP column; the column support is composed of crosslinked divinylbenzene, rather than a typical reversed phase column built on a silica support which can nonspecifically retain proteins. This denaturing and reductive technique cleanly separates the 6 species consisting of light chain with 0 and 1 drug (L0 and L1) and heavy chain with 0 through 3 drugs (H0 through H3). FIG. 1 shows the drug loading levels that can be observed for the various E4 species. Pure E4 from method 2b was separated by PLRP in FIG. 6. Unmodified light chain (L0) and heavy chain with two drugs (H2) are the species expected from 4F, while L1 and H1 are expected from 4A-D. Together with the Bioanalyzer, these data are consistent with method 1 producing about a 2:1 mixture of 4E to 4F while method 2b produces 2:1 4F to 4A-D. Thus using different chemical conditions, both the E4 yield and distribution of E4 isomers is significantly different between method 1 and 2b.

V. Compound Capable of Conjugation to Protein

A protein may be conjugated with any drug of interest, including a cytostatic agent or cytotoxic agent, an immunosuppressive agent, a toxin, a chelate, a compound, a molecule, a radionucleotide, or the like.

Cytotoxic Agents and Cytostatic Agents

Cytotoxic and cytostatic drugs include antibiotics (e.g., adriamycin), antitumor agents such as auristatins and auristatin derivatives, methotrexate, mitomycin C, daunorubicin, doxorubicin, and vinblastine, 5-fluorouracil DNA minor grove binders, DNA replication inhibitors, alkylating agents (e.g., platinum complexes such as cisplatin, mono(platinum), bis(platinum) and tri-nuclear platinum complexes and carboplatin), antiparasitic agents (e.g., pentamidine isethionate), anthracyclines, antifolates, antimetabolites, chemotherapy sensitizers, duocarmycins, etoposides, fluorinated pyrimidines, ionophores, lexitropsins, nitrosoureas, platinols, preforming compounds, purine antimetabolites, puromycins, radiation sensitizers, steroids, taxanes, topoisomerase inhibitors, vinca alkaloids, antimicrobial agents, antimicrotubule agents, or the like. When an antibody is conjugated to such a drug, it serves to direct the drug to the sites where the corresponding antigen occurs. Other agents and drugs which can be coupled to antibody are known, or can be easily ascertained, by those of skill in the art.

Individual cytotoxic or cytostatic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Other cytotoxic agents include, for example, dolastatins (see infra) DNA minor groove binders such as the enediynes (e.g., calicheamicin) and lexitropsins (see, also U.S. Pat. No. 6,130,237), duocarmycins, taxanes (e.g., paclitaxel and docetaxel), puromycins, CC-1065, SN-38, topotecan, morpholino-doxorubicin, rhizoxin, cyanomorpholino-doxorubicin, echinomycin, combretastatin, netropsin, epothilone A, B or D, estramustine, cryptophysins, cemadotin, maytansinoids, discodermolide, eleutherobin, and mitoxantrone.

In certain embodiments, the cytotoxic agent is a chemotherapeutic such as, for example, doxorubicin, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to proteins.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. patent application Ser. Nos. 09/845,786 (U.S. Patent Application Publication No. 20030083263) and 10/001,191; International Patent Application No. PCT/US03/24209: International Patent Application No. PCT/US02/13435: and U.S. Pat. Nos. 6,323, 315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In certain embodiments, the cytotoxic or cytostatic agent is an anti-tubulin agent. Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al. (1992), Cancer Res. 52:127131).

In some embodiments, the therapeutic agent is not a radioisotope.

In some embodiments, the cytotoxic or immunosuppressive agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscamet, or trifluridine.

In other embodiments, the cytotoxic or immunosuppressive agent is tacrolimus, cyclosporine or rapamycin. In further embodiments, the cytotoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Sargramostim, streptozocin, tamoxifen, temozolomide, teniposide, testolactone, thioguanine, toremifene, tretinoin, uracil mustard, valrubicin, vinblastine, vincristine, vinorelbine and zoledronate.

In some embodiments, the agent is an immunosuppressive agent. The immunosuppressive agent can be, for example, gancyclovir, tacrolimus, cyclosporine, rapamycin, cyclophosphamide, azathioprine, mycophenolate mofetil or methotrexate. Alternatively, the immunosuppressive agent can be, for example, a glucocorticoid (e.g., cortisol or aldosterone) or a glucocorticoid analogue (e.g., prednisone or dexamethasone).

In some embodiments, the immunosuppressive agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

Toxins

Toxins are usefully conjugated to antibodies specific for antigens associated with tumor, parasite or microbial cells. The toxin may be from, e.g., a plant (e.g., ricin or abrin), animal (e.g., a snake venom), or microbial (e.g., diphtheria or tetanus toxin).

Besides antibodies, the drugs or toxins may be conjugated to other carrier proteins, such as albumin.

Conjugation of Drugs to Protein

The drug has, or is modified to include, a group reactive with a conjugation point on the protein. For example, a drug can be attached by alkylation (e.g., at the ϵ-amino group of antibody lysines or the N-terminus of protein), reductive amination of oxidized carbohydrate, transesterification between hydroxyl and carboxyl groups, amidation at amino groups or carboxyl groups, and conjugation to thiols. For a examples of chemistries that can be used for conjugation, see, e.g., Current Protocols in Protein Science (John Wiley & Sons, Inc.), Chapter 15 (Chemical Modifications of Proteins) (the disclosure of which is incorporated by reference herein in its entirety.)

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

Sulfhydryl Reactive Agents

Sulfyhydryl reactive agents include alpha-haloacetyl compounds such as iodoacetamide, maleimides such as N-ethylmaleimide, mercury derivatives such as 3,6-bis-(mercurimethyl)dioxane with counter ions of acetate, chloride or nitrate, and disulfide derivatives such as disulfide dioxide derivatives, polymethylene bismethane thiosulfonate reagents and crabescein (a fluorescent derivative of fluorescein containing two free sulfhydryl groups which have been shown to add across disulfide bonds of reduced antibody).

Alpha-haloacetyl compounds such as iodoacetate readily react with sulfhydryl groups to form amides. These compounds have been used to carboxymethylate free thiols. They are not strictly SH specific and will react with amines. The reaction involves nucleophilic attack of the thiolate ion resulting in a displacement of the halide. The reactive haloacetyl moiety, X—CH$_2$ CO—, has been incorporated into compounds for various purposes. For example, bromotrifluoroacetone has been used for F-19 incorporation, and N-chloroacetyliodotyramine has been employed for the introduction of radioactive iodine into proteins.

Maleimides such as N-ethylmaleimide are considered to be fairly specific to sulfhydryl groups, especially at pH values below 7, where other groups are protonated. Thiols undergo Michael reactions with maleimides to yield exclusively the adduct to the double bond. The resulting thioether bond is very stable. They also react at a much slower rate with amino and imidazoyl groups. At pH 7, for example, the reaction with simple thiols is about 1,000 fold faster than with the corresponding amines. The characteristic absorbance change in the 300 nm region associated with the reaction provides a convenient method for monitoring the reaction. These compounds are stable at low pH but are susceptible to hydrolysis at high pH. See generally Wong, Chemistry of Protein Conjugation and Cross-linking; CRC Press, Inc., Boca Raton, 1991: Chapters 2 and 4).

A molecule (such as a drug) which is not inherently reactive with sulfhydryls may still be conjugated to the chemically activated proteins by means of a bifunctional crosslinking agent which bears both a group reactive with the molecule of interest and a sulfhydryl reactive group. This agent may be reacted simultaneously with both the molecule of interest (e.g., through an amino, carboxy or hydroxy group) and the chemically activated protein, or it may be used to derivatize the molecule of interest to form a partner molecule which is then sulfhydryl reactive by virtue of a moiety derived from the agent, or it may be used to derivatize the chemically activated protein to make it reactive with the molecule of interest.

Linkers

The drug can be linked to a protein by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

A linker can include a group for linkage to the protein. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio). See generally Wong, Chemistry of Protein Conjugation and Cross-linking; CRC Press, Inc., Boca Raton, 1991.

In certain embodiments, the antibody or protein drug conjugate can be of the following formula:

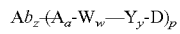

or pharmaceutically acceptable salts or solvates thereof.
wherein:
Ab is an antibody or other protein,
A is a stretcher unit,
a is 0 or 1,
each W is independently a linker unit,
w is an integer ranging from 0 to 12,
Y is a spacer unit, and
y is 0, 1 or 2,
p ranges from 1 to about 20, and
D is a drug, a label or other molecule.
z is the number of potential conjugation sites on the protein, wherein p<z.

In other embodiments, p can be, for example, 2, 4, 8, 10, 12, 16, 25, or more.

A stretcher unit can is capable of linking a linker unit to an antibody or other protein. The stretcher unit has a functional group that can form a bond with a functional group of the antibody or other protein. Useful functional groups include, but are not limited to, sulfhydryl (—SH), amino, hydroxyl, carboxy, the anomeric hydroxyl group of a carbohydrate, and carboxyl.

The linker unit is typically an amino acid unit, such as for example a dipeptide, tripeptide, tetrapeptide, pentapeptide, hexapeptide, heptapeptide, octapeptide, nonapeptide, decapeptide, undecapeptide or dodecapeptide unit. The linker unit can be cleavage or non-cleavable inside the cell.

A spacer unit, if present, links a linker unit to the drug. alternately, a spacer unit can link a stretcher unit to a drug moiety when the linker unit is absent. The spacer unit can also link a drug to an antibody or protein when both the linker unit and stretcher unit are absent.

VI. Conjugates and Their Uses

In Vitro Immunodiagnosis.

In one embodiment, a protein (e.g., an antibody) is conjugated to a detectable label for use in in vitro immunodiagnosis. The label may be a radiolabel, fluorophore, or enzyme which is directly or indirectly conjugatable to conjugation point (e.g., a free thiol group) of the chemically activated antibody. The sample may be of clinical (e.g., blood, urine, semen, or cerebrospinal fluid, or a solid tissue or organ) or non-clinical (e.g., soil, water, food) nature. The assay may be qualitative or quantitative, and in any desired format, including sandwich and competitive formats. Numerous immunoassay formats, labels, immobilization techniques, etc., are disclosed in the following publications, hereby incorporated by reference herein: O'Sullivan (1976), Annals Clin. Biochem. 16:221-240; McLaren (1981), Med. Lab. Sci. 38:245-51; Ollerich (1984), J. Clin. Chem. Clin. Biochem. 22:895-904; Ngo and Lenhoff (1982), Mol. Cell. Biochem., 44:3-12.

Immunoimaging.

An immunoconjugate may also be used for in vivo immunoimaging. For this purpose, the protein (e.g., an antibody) is labeled by means which permit external visualization of its position or location within a subject or part thereof, such as an organ. Typically, an immunoimaging agent will be an antibody labeled directly (as with Technetium) or indirectly (as with chelated Indium) with a suitable radioisotope. After injection into the patient, the location of the conjugate may be tracked by a detector sensitive to particles emitted by the radiolabel, e.g., a gamma-scintillation camera in the case of a gamma emitter.

Immunotherapy.

For immunotherapy, a protein can be conjugated to suitable drug, such as a cytotoxic or cytostatic agent, an immunosuppressive agent, a radioisotope, a toxin, or the like. The conjugate can be used for inhibiting the multiplication of a tumor cell or cancer cell, causing apoptosis in a tumor or cancer cell, or for treating cancer in a patient. The conjugate can be used accordingly in a variety of settings for the treatment of animal cancers. The conjugate can be used to deliver a drug to a tumor cell or cancer cell. Without being bound by theory, in some embodiments, the conjugate binds to or associates with a cancer-cell or a tumor-associated antigen, and the conjugate and/or drug can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the conjugate (e.g., in a linker) are hydrolytically cleaved by one or more tumor-cell or cancer-cell-associated proteases, resulting in release of the drug. The released drug is then free to migrate within the cell and induce cytotoxic or cytostatic or other activities. In some embodiments, the drug is cleaved from the antibody outside the tumor cell or cancer cell, and the drug subsequently penetrates the cell, or acts at the cell surface.

Thus, in some embodiments, the conjugate or other protein binds to the tumor cell or cancer cell. In some embodiments, the conjugate binds to a tumor cell or cancer cell antigen which is on the surface of the tumor cell or cancer cell. In other embodiments, the conjugate binds to a tumor cell or cancer cell antigen which is an extracellular matrix protein associated with the tumor cell or cancer cell.

The specificity of the protein for a particular tumor cell or cancer cell can be important for determining those tumors or cancers that are most effectively treated. For example, antibodies having an anti-CD30 or an anti-CD40 antibody or other binding protein can be useful for treating hematologic malignancies.

Other particular types of cancers that can be treated with the protein-drug conjugates include, but are not limited to, solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, blood-borne cancers (including but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma), acute and chronic leukemias (e.g., lymphoblastic, myelogenous, lymphocytic, and myelocytic leukemias), and Lymphomas (e.g., Hodgkin's disease, non-Hodgkin's Lymphoma, Multiple myeloma, Waldenström's macroglobulinemia, Heavy chain disease, and Polycythemia vera). The proteins provide conjugation-specific tumor or cancer targeting.

Multi-Modality Therapy for Cancer

As discussed above, cancers, including, but not limited to, a tumor, metastasis, or other disease or disorder characterized by uncontrolled cell growth, can be treated or prevented by administration of a protein-drug conjugate.

In other embodiments, methods for treating or preventing cancer are provided, including administering to a patient in need thereof an effective amount of a conjugate and a chemotherapeutic agent. In some embodiments, the chemotherapeutic agent is that with which treatment of the cancer has not been found to be refractory. In some embodiments, the chemotherapeutic agent is that with which the treatment of cancer has been found to be refractory. The conjugate can be administered to a patient that has also undergone an treatment, such as surgery for treatment for the cancer. In another embodiment, the additional method of treatment is radiation therapy.

In an exemplary embodiment, the protein-drug conjugate is administered concurrently with the chemotherapeutic agent or with radiation therapy. In another exemplary embodiment, the chemotherapeutic agent or radiation therapy is administered prior or subsequent to administration of the protein-drug conjugate, in one aspect at least an hour, five hours, 12 hours, a day, a week, a month, in further aspects several months (e.g., up to three months), prior or subsequent to administration of the conjugate.

A chemotherapeutic agent can be administered over a series of sessions. Any one or a combination of the chemotherapeutic agents listed below can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a protein-drug conjugate are provided as an alternative to chemotherapy or radiation therapy, where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The protein-drug conjugate can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of a conjugate with or without accompanying high dose radiation therapy, and the stem cell graft is infused back into the animal. Supportive care is then provided while bone marrow function is restored and the animal recovers.

Multi-Drug Therapy for Cancer

Methods for treating cancer include administering to a patient in need thereof an effective amount of an a protein-drug conjugate and another therapeutic agent that is an anticancer agent are disclosed. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel.

The anti-cancer agent includes, but is not limited to, a drug such as an alkylating agents such as a nitrogen mustard (e.g., cyclophosphamide, ifosfamide, trofosfamide, chlorambucil, melphalan), nitrosoureas (e.g., carmustine (BCNU), lomustine (CCNU)), alkylsulphonates (e.g., busulfan, treosulfan), triazenes (e.g., decarbazine), Platinum containing compounds (e.g., cisplatin, carboplatin); plant alkaloids, such as vinca alkaloids (e.g., vincristine, vinblastine, vindesine, vinorelbine), taxoids (e.g., paclitaxel, docetaxol); DNA topoisomerase inhibitors such as epipodophyllins (e.g., etoposide, teniposide, topotecan, 9-aminocamptothecin, camptothecin, crisnatol, mitomycins (e.g., mitomycin C); antimetabolites such as anti-folates such as DHFR inhibitors (e.g., methotrexate, trimetrexate), IMP dehydrogenase inhibitors (mycophenolic acid, tiazofurin, ribavirin, EICAR) and ribonucleotide reductase inhibitors (e.g., hydroxyurea, deferoxamine), pyrimidine analogs such as uracil analogs (5-fluorouracil, floxuridine, doxifluridine, ratitrexed), cytosine analogs (e.g., cytarabine (ara C), cytosine arabinoside, fludarabine), and purine analogs (e.g., mercaptopurine, thioguanine); hormonal therapies, such as receptor antagonists, such as anti-estrogens (e.g., tamoxifen, raloxifene, megestrol), LHRH agonists (e.g., goscrclin, leuprolide acetate), and anti-androgens (e.g., flutamide, bicalutamide; retinoids/deltoids such as vitamin D3 analogs (e.g., EB 1089, CB 1093, KH 1060), photodynamic therapies (e.g., vertoporfin (BPD-MA), phthalocyanine, photosensitizer Pc4, demethoxy-hypocrellin A (2BA-2-DMHA)), cytokines (e.g., interferon-α, interferon-γ, tumor necrosis factor), as well as other drugs, such as gemcitabine, velcade, revamid, thalamid, isoprenylation inhibitors (e.g., lovastatin), dopaminergic neurotoxins (e.g., 1-methyl-4-phenylpyridinium ion), cell cycle inhibitors (e.g., staurosporine), actinomycins (e.g., actinomycin D, dactinomycin), bleomycins, bleomycin A2, bleomycin B2, peplomycin), anthracyclines (daunorubicin, Doxorubicin (adriamycin), idarubicin, epirubicin, pirarubicin, zorubicin, mtoxantrone), MDR inhibitors (e.g., verapamil), and $Ca^{2+}$ ATPase inhibitors (e.g., thapsigargin)

Treatment of Autoimmune Diseases

The protein-drug conjugates are useful for killing or inhibiting the replication of a cell that produces an autoimmune disease or for treating an autoimmune disease. The conjugates can be used accordingly in a variety of settings for the treatment of an autoimmune disease in a patient. The conjugates can be used to deliver a drug to a target cell. Without being bound by theory, in one embodiment, the conjugates associate with an antigen on the surface of a target cell, and the conjugate is then taken up inside a target-cell through receptor-mediated endocytosis. Once inside the cell, one or more specific peptide sequences (e.g., within a linker) are enzymatically or hydrolytically cleaved, resulting in release of a drug. The released drug is then free to migrate in the cytosol and induce cytotoxic or cytostatic activities. In an alternative embodiment, the drug is cleaved from the conjugate outside the target cell, and the drug subsequently penetrates the cell.

In some embodiments, the protein-drug conjugate binds to an autoimmune antigen. In one aspect, the antigen is on the surface of a cell involved in an autoimmune condition. In some embodiments, an antibody binds to an autoimmune antigen which is on the surface of a cell. In an exemplary embodiment, an antibody binds to activated lymphocytes that are associated with the autoimmune disease state. In a further embodiment, the conjugates kill or inhibit the multiplication of cells that produce an autoimmune antibody associated with a particular autoimmune disease.

Particular types of autoimmune diseases that can be treated with the protein-drug conjugate include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis and tuberculosis); and activated B lymphocyte related disorders (e.g., systemic lupus erythematosus, Goodpasture's syndrome, rheumatoid arthritis and type I diabetes). Other autoimmune diseases include, but are not limited to, active chronic hepatitis, Addison's disease, allergic alveolitis, allergic reaction, allergic rhinitis, Alport's Syndrome, anaphlaxis, ankylosing spondylitis, anti-phospholipid syndrome, arthritis, ascariasis, aspergillosis, atopic allergy, atropic dermatitis, atropic rhinitis, Behcet's disease, Bird-Fancier's Lung, bronchial asthma, Caplan's syndrome, cardiomyopathy, Celiac disease, Chagas' disease, chronic glomerulonephritis, Cogan's Syndrome, cold agglutinin disease, congenital rubella infection, CREST syndrome, Crohn's disease, cryoglobulinemia, Cushing's syndrome, dermatomyositis, discoid lupus, Dressler's syndrome, Eaton-Lambert syndrome, echovirus infection, encephalomyelitis, endocrine opthalmopathy, Epstein-Barr virus infection, equine heaves, erythematosis, Evan's syndrome, Felty's syndrome, fibromyalgia, Fuch's cyclitis, gastric atrophy, gastrointestinal allergy, giant cell arteritis, glomerulonephritis, goodpasture's syndrome, graft v. host disease, Graves' disease, Guillain-Barre disease, Hashimoto's thyroiditis, hemolytic anemia, Henoch-Schonlein Purpura, idiopathic adrenal atrophy, idiopathic pulmonary fibritis, IgA nephropathy, inflammatory bowel disease, insulin-dependent diabetes mellitus, juvenile arthritis, juvenile diabetes mellitus (Type I), Lambert-Eaton syndrome, laminitis, lichen planus, lupoid hepatitis, lupus, lymphopenia, Meniere's disease, mixed connective tissue disease, multiple sclerosis, myasthenia gravis, pernicious anemia, polyglandular syndromes, presenile dementia, primary agammaglobulinemia, primary biliary cirrhosis, psoriasis, psoriatic arthritis, Raynauds phenomenon, recurrent abortion, Reiter's syndrome, rheumatic fever, rheumatoid arthritis, Sampter's syndrome, schistosomiasis, Schmidt's syndrome, scleroderma, Shulman's syndrome, Sjorgen's syndrome, stiff-man syndrome, sympathetic ophthalmia, systemic lupus erythematosis, Takayasu's arteritis, temporal arteritis, thyroiditis, thrombocytopenia, thyrotoxicosis, toxic epidermal necrolysis, Type B insulin resistance, Type I diabetes mellitus, ulcerative colitis, uveitis, vitiligo, Waldenstrom's macroglobulemia, and Wegener's granulomatosis.

Multi-Drug Therapy of Autoimmune Diseases

Methods for treating an autoimmune disease are also disclosed that include administering to a patient in need thereof an effective amount of a protein-drug conjugate alone or in combination another therapeutic agent known for the treatment of an autoimmune disease. The anti-autoimmune disease agent can include, but is not limited to, the following: cyclosporine, cyclosporine A, mycophenylate mofetil, sirolimus, tacrolimus, enanercept, prednisone, azathioprine, methotrexate, cyclophosphamide, aminocaproic acid, chloroquine, hydroxychloroquine, hydrocortisone, dexamethasone, chlorambucil, DHEA, danazol, bromocriptine, meloxicam and infliximab.

Treatment of Infectious Diseases

The protein-drug conjugates are useful for killing or inhibiting the multiplication of a cell that produces an infectious disease or for treating an infectious disease. The conjugates can be used accordingly in a variety of settings for the treatment of an infectious disease in a patient. The ADCs can be used to deliver a drug to a target cell. In one embodiment, the antibody binds to the infectious disease cell. In some embodiments, the conjugate kills or inhibit the multiplication of cells that produce a particular infectious disease. Particular types of infectious diseases that can be treated with the conjugates include, but are not limited to, the following: bacterial diseases, such as diphtheria, pertussis, occult bacteremia, urinary tract infection, gastroenteritis, cellulites, epiglottitis, tracheitis, adenoid hypertrophy, retropharyngeal abcess, impetigo, ecthyma, pneumonia, endocarditis, septic arthritis, pneumococcal, peritonitis, bactermia, meningitis, acute purulent meningitis, urethritis, cervicitis, proctitis, pharyngitis, salpingitis, epididymitis, gonorrhea, syphilis, listeriosis, anthrax, nocardiosis, salmonella, typhoid fever, dysentery, conjunctivitis, sinusitis, brucellosis, tularemia, cholera, bubonic plague, tetanus, necrotizing enteritis, and actinomycosis; mixed anaerobic infections, such as syphilis, relapsing fever, leptospirosis, Lyme disease, rat bite fever, tuberculosis, lymphadenitis, leprosy, chlamydia, chlamydial pneumonia, trachoma, and inclusion conjunctivitis; systemic fungal diseases such as histoplamosis, coccidiodomycosis, blastomycosis, sporotrichosis, cryptococcsis, systemic candidiasis, aspergillosis, mucormycosis, mycetoma, and chromomycosis; rickettsial diseases such as typhus, Rocky Mountain Spotted Fever, ehrlichiosis, Eastern Tick-Borne Rickettsioses, rickettsialpox, Q fever and bartonellosis; parasitic diseases such as malaria, babesiosis, African sleeping sickness, Chagas' disease, leishmaniasis, Dum-Dum fever, toxoplasmosis, meningoencephalitis, keratitis, entamebiasis, giardiasis, cryptosporidiosis, isosporiasis, cyclosporiasis, microsporidiosis, ascariasis, whipworm infection, hookworm infection, threadworm infection, ocular larva migrans, trichinosis, Guinea worm disease, lymphatic Filariasis, loiasis, River Blindness, canine heartworm infection, schistosomiasis, swimmer's itch, Oriental lung fluke, Oriental liver fluke, fascioliasis, fasciolopsiasis, opisthorchiasis, tapeworm infections, hydatid disease, and alveolar hydatid disease; viral diseases such as measles, subacute sclerosing panencephalitis, common cold, mumps, rubella, roseola, Fifth Disease, chickenpox, respiratory syncytial virus infection, croup, bronchiolitis, infectious mononucleosis, poliomyelitis, herpangina, hand-foot-and-mouth disease, Bornholm disease, genital herpes, genital warts, aseptic meningitis, myocarditis, pericarditis, gastroenteritis, acquired immunodeficiency syndrome (AIDS), human immunodeficiency virus (HIV), Reye's syndrome, Kawasaki syndrome, influenza, bronchitis, viral "Walking" pneumonia, acute febrile respiratory disease, acute pharyngoconjunctival fever, epidemic keratoconjunctivitis, Herpes Simplex Virus 1 (HSV-1), Herpes Simplex Virus 2 (HSV-2), shingles, cytomegalic inclusion disease, rabies, progressive multifocal leukoencephalopathy, kuru, fatal familial insomnia, Creutzfeldt-Jakob disease, Gerstmann-Straussler-Scheinker disease, tropical spastic paraparesis, western equine encephalitis, California encephalitis, St. Louis encephalitis, Yellow Fever, Dengue, lymphocytic choriomeningitis, Lassa fever, hemorrhagic fever, Hantvirus pulmonary syndrome, Marburg virus infections, Ebola virus infections and smallpox.

Multi-Drug Therapy of Infectious Diseases

Methods for treating an infectious disease are disclosed as including administering to a patient in need thereof a protein-drug conjugate alone or in combination with another therapeutic agent that is an anti-infectious disease agent. The anti-infectious disease agent can be, but not limited to, the following: β-lactam antibiotics, such as penicillin G, penicillin V, cloxacillin, dicloxacillin, methicillin, nafcillin, oxacillin, ampicillin, amoxicillin, bacampicillin, azlocillin, carbenicillin, mezlocillin, piperacillin and ticarcillin; aminoglycosides such as amikacin, gentamicin, kanamycin, neomycin, netilmicin, streptomycin and tobramycin; macrolides such as azithromycin, clarithromycin, erythromycin, lincomycin and clindamycin; tetracyclines such as demeclocycline, doxycycline, minocycline, oxytetracycline and tetracycline; quinolones such as cinoxacin, and nalidixic acid; fluoroquinolones such as ciprofloxacin, enoxacin, grepafloxacin, levofloxacin, lomefloxacin, norfloxacin, ofloxacin, sparfloxacin and trovafloxicin; polypeptides such as bacitracin, colistin and polymyxin B; sulfonamides such as sulfisoxazole, sulfamethoxazole, sulfadiazine, sulfamethizole and sulfacetamide; and other antibacterial agents, such as trimethoprim, sulfamethazole, chloramphenicol, vancomycin, metronidazole, quinupristin, dalfopristin, rifampin, spectinomycin and nitrofurantoin; and antiviral agents, such as general antiviral agents such as idoxuradine, vidarabine, trifluridine, acyclovir, famcicyclovir, pencicyclovir, valacyclovir, gancicyclovir, foscarnet, ribavirin, amantadine, rimantadine, cidofovir; antisense oligonucleotides, immunoglobulins and interferons; and drugs for HIV infection such as tenofovir, emtricitabine, zidovudine, didanosine, zalcitabine, stavudine, lamivudine, nevirapine, delavirdine, saquinavir, ritonavir, indinavir and nelfinavir.

VII. Pharmaceutical Compositions

In in vivo use, generally, whether for immunoimaging, for immunotherapy or by other uses, the conjugate is introduced into a subject. The composition can comprise a single isomer, or one or more partially-loaded isomers, of the conjugate. For example, if the protein is an antibody, the composition can comprise a single E2, E4 or E6 isomer, a mixture of selected E2, E4 or E6 isomers, all E2, E4 or E6 isomers alone, or a mixture of E2, E4 and E6 isomers. In some embodiments, a composition containing a certain isomer(s) can be substantially free of other isomers. In this context, "substantially free" means the composition contains less than about 20%, less than about 10%, less than about 5% less than about 2% or less than about 1% of the other isomers.

The compositions can be in any form that allows for the composition to be administered to a patient. For example, the composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In one aspect, the compositions are administered parenterally. In yet another aspect, the conjugate or compositions are administered intravenously.

The conjugate can be introduced by injection. Typically, the conjugate is administered intravascularly (intravenously or intraarterially) or intrathetically, often by infusion. In addition, in appropriate cases the conjugate may be introduced subcutaneously, submucosally, intramuscularly, intracranially, or by other accepted routes of drug administration.

In other embodiments, the composition includes an effective amount of a conjugate and a pharmaceutically acceptable carrier or vehicle. Such compositions are suitable for veterinary or human administration.

Pharmaceutical compositions can be formulated so as to allow a conjugate to be bioavailable upon administration of the composition to a patient. Compositions can take the form of one or more dosage units, where for example, a tablet can be a single dosage unit, and a container of a conjugate in injectable form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the conjugate, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins; disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The amount of the conjugate that is effective in the treatment of a particular disorder or condition will depend on the nature of the disorder or condition, and can be determined by standard clinical techniques. The dosage ranges for the administration of the disclosed protein-drug conjugates are those large enough to produce the desired effect in which the symptoms of the condition or disorder are ameliorated. The dosage should not be so large as to cause adverse side effects, such as unwanted cross-reactions, anaphylactic reactions, and the like. In addition, in vitro or in vivo assays can optionally be employed to help identify optimal dosage ranges.

The precise dose to be employed in the compositions will also depend on the age, condition, sex and extent of the disease in the patient, route of administration, and the seriousness of the disease or disorder, and should be decided according to the judgment of the practitioner and each patient's circumstances.

The compositions comprise an effective amount of a conjugate such that a suitable dosage will be obtained. Typically, this amount is at least about 0.01% of a conjugate by weight of the composition. When intended for oral administration, this amount can be varied to range from about 0.1% to about 80% by weight of the composition. In one aspect, oral compositions can comprise from about 4% to about 50% of the conjugate by weight of the composition. In yet another aspect, present compositions are prepared so that a parenteral dosage unit contains from about 0.01% to about 2% by weight of the conjugate.

For intravenous administration, the composition can comprise from about 0.01 to about 100 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of the conjugate.

Generally, the dosage of an conjugate administered to a patient is typically about 0.01 mg/kg to about 2000 mg/kg of the animal's body weight. In one aspect, the dosage administered to a patient is between about 0.01 mg/kg to about 10 mg/kg of the animal's body weight. In another aspect, the dosage administered to a patient is between about 0.1 mg/kg and about 250 mg/kg of the animal's body weight. In yet another aspect, the dosage administered to a patient is between about 0.1 mg/kg and about 20 mg/kg of the animal's body weight. In yet another aspect the dosage administered is between about 0.1 mg/kg to about 10 mg/kg of the animal's body weight. In yet another aspect, the dosage administered is between about 1 mg/kg to about 10 mg/kg of the animal's body weight.

The conjugates can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a conjugate or composition. In certain embodiments, more than one conjugate or composition is administered to a patient.

In specific embodiments, it can be desirable to administer one or more conjugates or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more conjugates or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In yet another embodiment, the conjugates can be delivered in a controlled release system, such as but not limited to, a pump or various polymeric materials can be used. In yet another embodiment, a controlled-release system can be placed in proximity of the target of the conjugates, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

In some embodiments, a protein conjugate can be combined with a carrier to form a compostion. The term "carrier" refers to a diluent, adjuvant or excipient, with which a conjugate is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the conjugate or compositions and pharmaceutically acceptable carriers are sterile. Water is an exemplary carrier when the conjugate are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The compositions, if desired, can also contain minor amounts of wetting or emulsifying agents, or pH buffering agents.

The compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

In an exemplary embodiment, the conjugate is formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The compositions can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of a conjugate of from about 0.05% to about 50% w/v (weight per unit volume of composition), in another aspect, from 0.1% to 10% w/v.

The composition can be intended for rectal administration, in the form, e.g., of a suppository which will melt in the rectum and release the conjugate.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients.

Whether in solid, liquid or gaseous form, the present compositions can include a pharmacological agent used in the treatment of cancer, an autoimmune disease or an infectious disease.

VIII. Pharmokinetics

In vivo characterization of the toxicity and efficacy of purified 4 drug conjugates of cAC10-vcMMAE in mice has been performed and are discussed in more detail in the Examples (see e.g., Examples 8 and 9). Briefly, these studies have shown that mixtures with an average of 4 drugs per antibody are equally efficacious as those conjugates with 8 drugs (single dose of 1 mg/Kg for both), while being less toxic (MTD of 100 mg/Kg for 4 drugs per antibody versus 50 mg/Kg for 8 drugs per antibody). The purified material with 4 drugs per antibody from the DTT method is similar in efficacy and toxicity, while purified material with 4 drugs per antibody from the DTNB method has a slightly higher MTD of 120 mg/Kg while being efficacious at half the dose of the other conjugates (0.5 mg/Kg).

Loading cAC10 with two, four, or eight drugs per antibody had no effect on the binding to the target antigen CD30. The in vitro potency of the cAC10-ADCs was directly dependent on drug loading, and thus the total MMAE exposure.

cAC10-E4 demonstrated comparable anti-tumor activity to cAC10-E8 in a Karpas-299 xenograft model at the same dose of antibody, half the MMAE dose. Based on the in vitro finding that potency was directly related to drug loading, the equivalent in vivo anti-tumor activity of cAC10-E4 and cAC10-E8 was unanticipated. Investigation of the pharmacokinetics of the ADCs revealed that clearance was directly related to the drug loading of the ADCs and exposure (Area Under the Curve—AUC) was inversely related to drug loading. The AUC of cAC10-E4 was 3-fold higher than cAC10-E8. The larger AUC of cAC10-E4 compared to cAC10-E8 was apparently sufficient to compensate for the reduced potency, leading to equivalent efficacy. Attempts to improve efficacy by decelerating the plasma elimination half-life to augment AUCs have been accomplished by methods including the construction of albumin fusion proteins for interferon-$\alpha$ and liposomal delivery of the anti-cancer drug Lurtotecan. Unlike these examples where the objective was to lengthen the plasma half-life, the enhanced exposure of cAC10-E4 was a valuable consequence of reducing MMAE loading.

As disclosed in Example 8, dosing cAC10-E2 with 1.0 mg/kg/dose q4d×4 yielded ten out of ten cures. While cAC10-E2 did not demonstrate equivalent anti-tumor activity compared to cAC10-E4 at the same mAb dose, the dose of cAC10-E2 to achieve equivalent anti-tumor activity compared to cAC10-E4 is probably less than two-fold, based on the in vivo efficacy experiments. Similar to cAC10-E4, the improved exposure of cAC10-E2 may play a significant part in compromising the lower in vitro potency.

To maximize the therapeutic potential of cAC10-Val-Cit-MMAE ADCs, a high therapeutic index is needed. Reducing the amount of MMAE molecules per mAb from eight to four enhanced the therapeutic index from 100 to 200. Given steep dose-response curves of chemotherapeutic reagents a two-fold difference in therapeutic index may be significant in terms of the overall clinical implications with regards to toxicities.

By reducing the quantity of MMAE from eight to four molecules per mAb, there was a decrease of in vitro activity, yet a demonstrated equivalent anti-tumor activity in vivo. While a further reduction in drug loading to two MMAE molecules per antibody further reduced the in vitro activity, cAC10-E2 had equivalent or better efficacy than cAC10-E4 and cAC10-E8 at double the dose in a multi-dose setting. The therapeutic window was increased two-fold by reducing drug loading from eight MMAE molecules to four, and at the very least maintained with a further reduction to two drugs per antibody. There is considerable value in optimizing drug substitution of ADCs.

EXAMPLES

Example 1 of Method 1 cAC10 was partially reduced with limited concentration of DTT as follows: cAC10 (8 mg/mL or 53.8 μM) was treated with 3.5 molar equivalents of DTT (188.4 μM; Sigma) in 0.05 M sodium borate pH 8, 0.05 M NaCl, and 1 mM diethylenetriaminepentaacetic acid (DTPA; Aldrich) for 1 h at 37° C. The reduced antibody was then purified by desalting on a PD-10 column (Amersham Biosciences). The PD-10 column was equilibrated with 25 mL of phosphate buffered saline (PBS) pH 7.4 (GIBCO) with 1 mM DTPA (PBSD), 1 mL of the above solution applied to the column, the column washed with 1.8 mL of PBSD, and the column eluted with 1.4 mL of PBSD. The protein concentration was quantitated using an absorbance value of 1.58 at 280 nm for a 1.0-mg/mL solution, and the molar concentration determined using a molecular weight of 150,000 g/mol. The concentration of antibody-cysteine thiols produced was determined by titrating with 5,5'-dithio-bis-(2-nitrobenzoic acid) (DTNB; Pierce), typically resulting in slightly higher than 4 antibody-cysteine thiols per antibody using this method.

The drug vcMMAE was then conjugated to reduced cAC10 as follows: reduced cAC10 (typically 30 μM antibody and 120 μM antibody-cysteine thiols final concentration) was first cooled to 0° C. vcMMAE was dissolved in cold acetonitrile and rapidly mixed with the antibody solution. The final acetonitrile concentration was 20%, while the final drug concentration was 135 to 150 μM (4.5 to 5 molar equivalents, which is a slight excess over the antibody-cysteine thiols). This solution was allowed to incubate for 30 min at 0° C., the excess vcMMAE quenched with cysteine (1 mM final concentration), and the conjugate purified using a PD-10 column as described above.

Example 2 of Method 1 cAC10 with 4 vcMMAE per antibody (E4 mix) was prepared with limiting amounts of DTT as follows: cAC10 was treated with 3.25 molar equivalents of DTT in 0.025 M sodium borate pH 8, 0.025 M NaCl, 1 mM DTPA for 2 h at 37° C. This mixture was diluted 5 fold with water and applied to a hydroxyapatite column (Macroprep ceramic type I 40 µm, BioRad, Hercules, Calif.) at a flow rate of 10 mL/min. The column size was 1 mL per 10 mg of cAC10. The column was previously equilibrated with 5 column volumes of 0.5 M sodium phosphate pH 7, 10 mM NaCl and 5 column volumes of 10 mM sodium phosphate pH 7, 10 mM NaCl. Following application, the column was washed with 5 column volumes of 10 mM sodium phosphate pH 7, 10 mM NaCl and then eluted with 100 mM sodium phosphate pH 7, 10 mM NaCl. DTPA was added to 1 mM following elution. The protein concentration was quantitated using an absorbance value of 1.58 at 280 nm for a 1.0-mg/mL solution, and the molar concentration determined using a molecular weight of 148, 449 g/mol. The concentration of antibody-cysteine thiols produced was determined by titrating with DTNB, typically resulting in 4.0 to 4.5 thiols per antibody.

Reduced cAC10 was alkylated with a slight excess of vcMMAE over antibody-cysteine thiols (1.1 molar equivalents). To keep the vcMMAE soluble, 10% DMSO was present in the final reaction mixture. Alternatively, the vcMMAE could be kept in a solution comprising 5% by volume of an alcohol, such as ethanol and isopropyl alcohol. The alkylation reaction was performed at 0° C. for 30 min. Cysteine (1 mM final) was used to quench any unreacted vcMMAE. cAC10-vcMMAE was purified by hydroxyapatite chromatography as described above. Following elution, the buffer was changed to phosphate buffered saline (Invitrogen, Carlsbad, Calif.) using Amicon (Millipore, Bedford, Mass.) Ultrafree 30K cutoff spin concentration devices. The protein concentration was quantitated using an absorbance value of 1.62 at 280 nm for a 1.0-mg/mL solution.

Example 3 of Method 2a cAC10 was fully reduced by adding a large excess of DTT. The final reaction concentrations were 8 mg/mL cAC10, 0.05 M sodium borate pH 8, 0.05 M NaCl, 10 mM DTT, and 1 mM DTPA. This solution was incubated at 37° C. for 30 min and the antibody purified by desalting on a PD-10 column as described above. Slightly more than 8 antibody-cysteine thiols as determined by DTNB titration were produced using these conditions.

Partial reoxidation was achieved using DTNB as an oxidizing agent. Reduced cAC10 (typically 30 µM) was cooled to 0° C. and then treated with 1.5 to 2.5 molar equivalents of DTNB (45 to 75 µM final concentration; the highest yields of E4 were obtained using 2.0 equivalents). The solution was rapidly mixed by inversion and allowed to incubate at 0° C. for 10-20 min. The extent of reaction can be observed since the released TNB⁻ is yellow. Typically, the reaction appeared to be complete within a few seconds. Cysteine was added (1 mM final concentration) to ensure that all TNB was present as TNB⁻ rather than in mixed disulfides with antibody cysteines. The antibody was then purified on a PD-10 column or a hydroxylapatite column as described above. Typically 4 antibody-cysteine thiols were observed by DTNB titration following this partial reoxidation procedure. The vcMMAE drug was finally conjugated to these antibody-cysteine thiols and purified by PD-10 as described above for method 1.

Example 4 of Method 2b

Fully reduced cAC10 was prepared as described above for method 2a. Fully reduced cAC10 (typically 30 µM) was cooled to 0° C. and then treated with 1.5 to 2.5 equivalents of DTNB (45 to 75 µM final concentration). The solution was rapidly mixed by inversion and allowed to incubate at 0° C. for 10 min. Without further purification, the partially reoxidized cAC10 was then rapidly mixed with 5 equivalents vcMMAE dissolved in cold acetonitrile. As with method 1, the final concentration of acetonitrile was 20%. In the conjugation reaction, the cAC10 final concentration was 24 µM (96 µM antibody-cysteine thiols or 4 per antibody) and the final vcMMAE concentration was 120 µM (5 molar equivalents). This solution was incubated for 30 min at 0° C. before quenching with cysteine and purifying by PD-10 as described above.

Preparative purification of E4 mix by hydroxyapatite. The buffer of cAC10 (25 mM sodium citrate pH 6.5, 250 mM NaCl, and 0.02% Tween-80) was changed to PBS using several 15 mL Amicon Ultrafree 30K cutoff spin concentration devices. 1.09 g of cAC10 in PBS was fully reduced with DTT in a final volume of 89 mL as follows: cAC10 (82.3 µM) was treated with 10 mM DTT in 0.025 M sodium borate pH 8, 0.025 M NaCl for 1 h at 37° C. This mixture was diluted to 250 mL with water and applied to a 70 mL hydroxyapatite column (Macroprep ceramic type I 40 µm, BioRad) at a flow rate of 10 mL/min. The column was previously equilibrated with 5 column volumes of 0.5 M sodium phosphate pH 7, 10 mM NaCl and 5 column volumes of 10 mM sodium phosphate pH 7, 10 mM NaCl. Following application, the column was washed with 5 column volumes of 10 mM sodium phosphate pH 7, 10 mM NaCl and then eluted with 100 mM sodium phosphate pH 7, 10 mM NaCl.

Fully reduced cAC10 was reoxidized with DTNB as follows: eluted material from above (6.02 mg/mL or 40.2 µM, 1.02 g in 170 mL) was cooled to 0° C. and then treated with 2.0 equivalents of DTNB (10 mM stock) for 20 min. Without further purification, reoxidized cAC10 was conjugated to vcMMAE. Cold cAC10 (31.9 µM final) was treated with 5 equivalents of vcMMAE (159.5 µM final) dissolved in DMSO (20% final) in a final volume of 214 mL. After 40 min at 0° C., 1.07 mL of 100 mM cysteine was added to quench any unreacted vcMMAE and the mixture was diluted to 750 mL with water. The conjugate was purified on a hydroxyapatite column as described above for the DTT reduction. The recovered cAC10-vcMMAE E4 mix (0.99 g, or 91% overall yield based on cAC10) was concentrated and the buffer changed to PBS using several 15 mL Amicon Ultrafree 30K cutoff spin concentration devices.

Preparative purification of pure E4 by HIC was performed on a 45 mL Toyopearl phenyl 650M HIC column at a flow rate of 10 mL/min at ambient temperature. Solvent A was 2 M NaCl and 50 mM sodium phosphate pH 7. Solvent B was 80% v/v 50 mM sodium phosphate pH 7 and 20% v/v acetonitrile. The column was previously equilibrated with 5 column volumes of solvent A. Up to 400 mg of cAC10-vcMMAE E4 mix purified by hydroxyapatite (above) was mixed with 1 volume of 4 M NaCl and 50 mM sodium phosphate pH 7 and applied to the column. E0 was not retained by the column. The different drug loaded species were eluted by sequential step gradients: E2 was eluted with 35% solvent B, E4 was eluted with 70% solvent B, E6 was eluted with 95% solvent B, and E8 was eluted with 100% solvent B. Purified E4 was concentrated and the buffer changed to PBS using several 15 mL Amicon Ultrafree 30K cutoff spin concentration devices, yielding 235 mg of pure E4 from two 400 mg purifications. Purity analysis by analytical HIC (below) showed E4 purity greater than 90%.

Example 5 of Method 1

Figure 8:
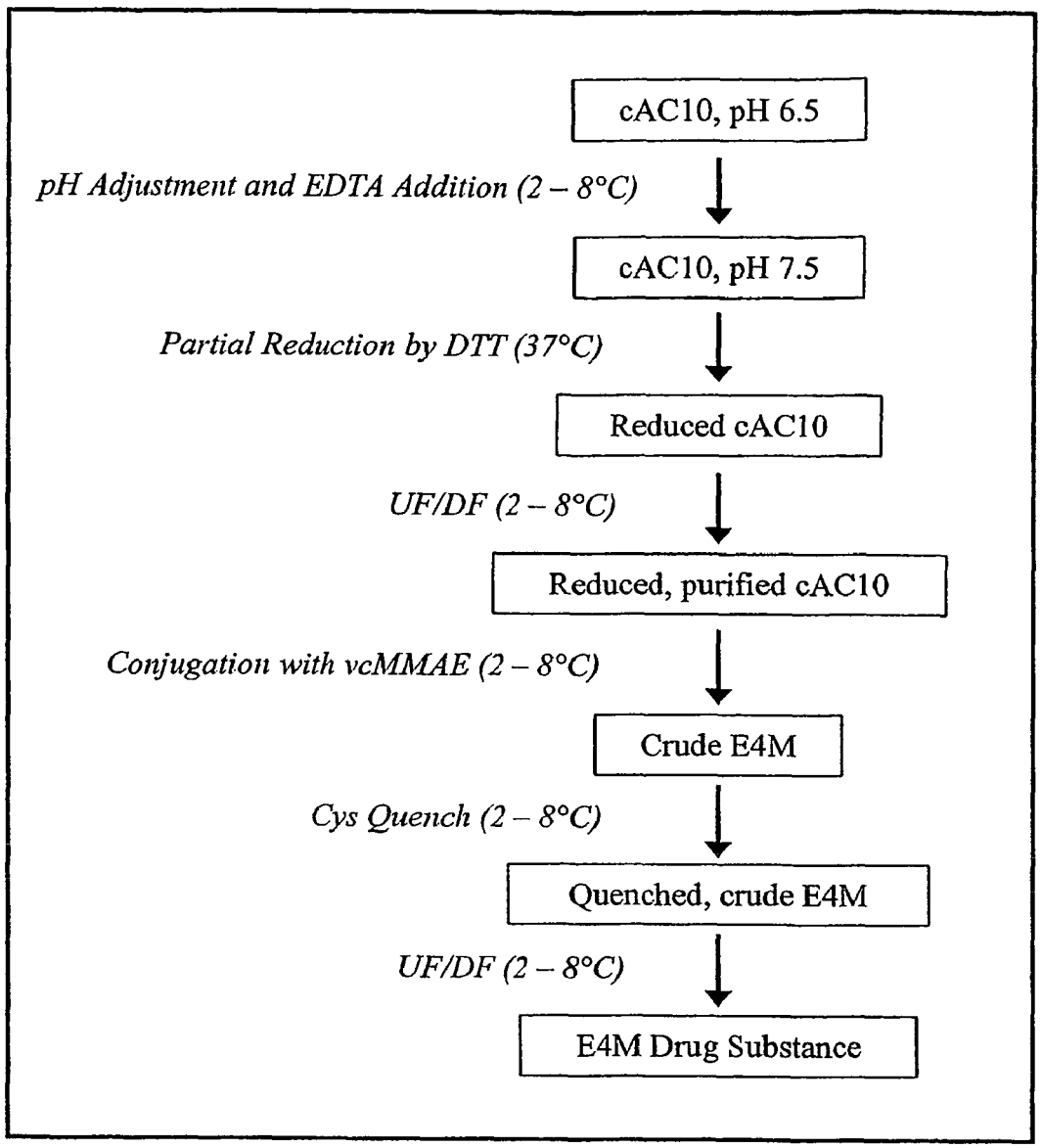
FIG. 8 is a process flow diagram for one aspect of a "Partial Reduction" conjugation process using DTT to produce E4 mixed isomers (E4M). The pH of the cAC10 antibody is adjusted to 7.5 with sodium phosphate dibasic and EDTA is added to a final concentration of 5 mM. The antibody solution is then heated to 37° C. To partially reduce the antibody, 2.95 molar equivalents of DTT is added to the antibody solution and allowed to reduce for 105 min at 37° C. After reduction, the antibody solution is cooled down to 2-8° C. and the excess DTT removed by constant-volume ultrafiltration/-diafiltraton (UF/DF) to obtain the reduced, purified cAC10. A sample of the reduced, purified cAC10 is taken and the thiol concentration, the antibody concentration, and the thiol-to-antibody molar ratio determined by A280 and DTNB tests. A slight excess of the drug-linker vcMMAE (typically 2-15% excess in the form of a DMSO solution) is then added into the antibody solution to start the conjugation reaction. The conjugation reaction is allowed to proceed for 30 min at 2-8° C. to obtain the crude E4M. At the end of the conjugation reaction, any excess vcMMAE drug-linker is quenched by reacting with a large excess of cysteine for 15 min at 2-8° C. to obtain the quenched, crude E4M. Buffer-exchange and removal of free drug and other small-molecule species is performed by constant-volume UF/DF (typically 6-10 diavolumes) to obtain the E4M drug substance.
Figure 9:
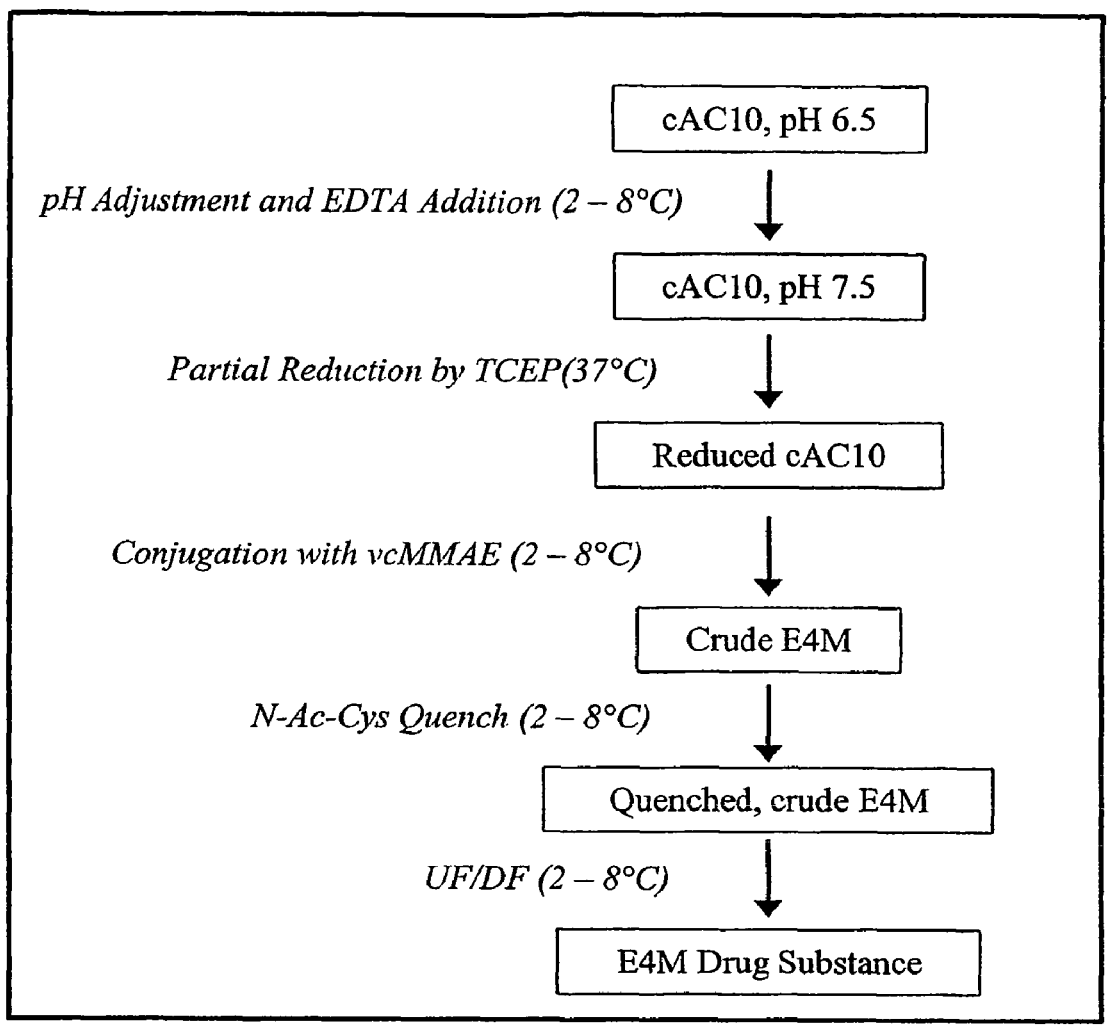
FIG. 9 is a process flow diagram for another aspect of a "Partial Reduction" conjugation process using TCEP, in which an intermediate purification step is not used, to produce E4 mixed isomers (E4M). The pH of the cAC10 antibody is adjusted to 7.5 with sodium phosphate dibasic and EDTA is added to a final concentration of 5 mM. The antibody solution is then heated to 37° C. To partially reduce the antibody, 2.20 molar equivalents of TCEP is added to the antibody solution and allowed to reduce for 105 min at 37° C. A sample of the reduction reaction is taken and the thiol concentration, the antibody concentration, and the thiol-to-antibody molar ratio determined by A280 and DTNB tests. After reduction, the antibody solution is cooled down to 2-8° C. A slight excess of the drug-linker vcMMAE (typically 2-15% excess in the form of a DMSO solution) is then added into the antibody solution to start the conjugation reaction. The conjugation reaction is allowed to proceed for 20 min at 2-8° C. to obtain the crude E4M. At the end of the conjugation reaction, any excess vcMMAE drug-linker is quenched by reacting with a large excess of N-acetyl cysteine for 20 min at 2-8° C. to obtain the quenched, crude E4M. Buffer-exchange and removal of free drug and other small-molecule species is performed by constant-volume UF/DF (typically 6-10 diavolumes) to obtain the E4M drug substance.

TCEP limited reduction followed by alkylation without intermediate purification was accomplished by treating cAC10 with 2.75 molar equivalents of TCEP in 0.025 M sodium borate pH 8, 0.025 M NaCl, 1 mM DTPA for 2 h at 37° C. See also FIG. 9 The mixture was then cooled to 0° C., and partially reduced cAC10 was alkylated with vcMMAE as described above. cAC10-vcMMAE was desalted using PD-10 columns (Amersham Biosciences, Piscataway, N.J.) equilibrated with phosphate buffered saline. (Partial reduction can also be performed with an intermediate purification step of the partially reduced antibody, as shown in FIG. 8.)

The samples used to determine the kinetics of isomer distribution were prepared as follows: cAC10 was reduced with 3.0 equivalents of DTT in 50 mM sodium phosphate pH 7.5 and 5 mM EDTA at 37° C. At the indicated time points, samples were removed, quenched with an equal volume of 200 mM sodium citrate pH 5, and purified using PD-10 columns equilibrated with phosphate buffered saline containing 5 mM EDTA. Reduced cAC10 was treated with vcMMAE as previously described and purified using PD-10 columns equilibrated with phosphate buffered saline.

Purification of E2, E4, and E6 pure by HIC was performed on a Toyopearl phenyl 650M HIC column (Tosoh Biosciences, Montgomeryville, Pa.) at a flow rate of 10 mL/min at ambient temperature. The column size was 1 mL per 7.5 mg of cAC10-vcMMAE. Solvent A was 2.0 M NaCl and 50 mM sodium phosphate pH 7. Solvent B was 80% v/v 50 mM sodium phosphate pH 7 and 20% v/v acetonitrile. The column was previously equilibrated with 5 column volumes of solvent A. cAC10-vcMMAE was mixed with 0.67 volume of 5 M NaCl (2.0 M final) and applied to the column. E0 was not retained by the column. The different drug loaded species were eluted by sequential step gradients: E2 was eluted with 35% solvent B, E4 was eluted with 70% solvent B, E6 was eluted with 95% solvent B, and E8 was eluted with 100% solvent B. Purified E4 was concentrated and the buffer changed to phosphate buffered saline using Amicon Ultrafree 30K cutoff spin concentration devices.

Example 6 of Analytical Methods

Drug loading was determined by measuring the ratio of the absorbance at 250 and 280 nm (A250/280). The number of vcMMAE per cAC10 has been empirically determined to be (A250/280-0.36)/0.0686.

The conjugates were analyzed for percent E4 purity by hydrophobic interaction chromatography (HIC) using a Tosoh Bioscience Ether-5PW column (part 08641) at a flow rate of 1 mL/min and a column temperature of 30° C. Solvent A was 50 mM sodium phosphate pH 7 and 2 M NaCl. Solvent B was 80% 50 mM sodium phosphate pH 7, 10% 2-propanol, and 10% acetonitrile. Isocratic 0% B for 15 min, a 50-min linear gradient from 0 to 100% B, a 0.1-min linear gradient from 100 to 0% B, and isocratic 0% B for 14.9 min. Injections (typically 90-100 µL) were 1 volume of purified vcMMAE-cAC10 conjugate (concentration of at least 3 mg/mL) and 1 volume of 50 mM sodium phosphate pH 7 and 4 M NaCl.

The ADC's, including pure E4 from HIC chromatography, were analyzed under denaturing and non-reducing conditions using an Agilent Bioanalyzer. A protein 200 chip was used under denaturing but nonreducing conditions as described by the manufacturer. Briefly, 4 µL of 1 mg/mL cAC10-vcMMAE was mixed with 2 µL of nonreducing loading buffer and heated to 100° C. for 5 min. Water (84 µL) was added and 6 µL of this mixture was loaded into each well of the chip.

Pure E4 was finally analyzed on a PLRP-S column (Polymer Laboratories). The flow rate was 1 mL/min and the column temperature was 65° C. Solvent A was 0.05% trifluoroacetic acid in water and solvent B was 0.04% trifluoroacetic acid in acetonitrile. Isocratic 25% B for 3 min, a 15-min linear gradient to 50% B, a 2-min linear gradient to 95% B, a 1-min linear gradient to 25% B, and isocratic 25% B for 2 min. Injections were µL of cAC10-vcMMAE previously reduced with 20 mM DTT at 37° C. for 20 min to cleave the interchain disulfides.

The ADC's also were analyzed under denaturing and reducing conditions on a PLRP-S column (Polymer Laboratories) (2.1×150 mm, 8µ, 1000 Å). The flow rate was 1 mL/min and the column temperature was 80° C. Solvent A was 0.050% trifluoroacetic acid in water and solvent B was 0.04% trifluoroacetic acid in acetonitrile. Isocratic 25% B for 3 min, a 25-min linear gradient to 50% B, a 2-min linear gradient to 95% B, a 1-min linear gradient to 25% B, and isocratic 25% B for 2 min. Injections were 10-20 µL of 1 mg/ml cAC10-vcMMAE previously reduced with 20 mM DTT at 37° C. for 15 min to cleave the remaining interchain disulfides. The mole fraction of each chain was determined using the following molar extinction coefficients: light chain with 0 vcMMAE: 30,160 $M^{-1}$ $cm^{-1}$; light chain with 1 vcMMAE: 31,660 $M^{-1}$ $cm^{-1}$; heavy chain with 0 vcMMAE: 86,915 $M^{-1}$ $cm^{-1}$; heavy chain with 1 vcMMAE: 88,415 $M^{-1}$ $cm^{-1}$; heavy chain with 2 vcMMAE: 89,915 $M^{-1}$ $cm^{-1}$; heavy chain with 3 vcMMAE: 91,415 $M^{-1}$ $cm^{-1}$.

The isomeric distribution for E2 and E6 was determined using solely PLRP-S HPLC data. For E2 isomer A (for these analyses, "isomer A" refers to both isomers 2A and 2B of FIG. 7), the mole fraction of light chain with 0 vcMMAE (L0) is equal to the mole fraction of heavy chain with 1 vcMMAE (H1), while for E2 isomer C, the mole fraction of light chain with 0 and 1 vcMMAE and the mole fraction of heavy chain with 0 and 1 vcMMAE are all equal. Since only light chain with 1 vcMMAE (L1) and heavy chain with 0 vcMMAE (H0) contribute to the percentage of isomer C, the percent isomer C can be expressed as follows:

$$\% C = 2L1 + 2H0 \quad (1)$$

The percent of isomer A is assumed to be 100-% C. Small amounts (less than 3% total) of heavy chain with 2 or 3 vcMMAE are often observed in the PLRP-S HPLC data. These are probably due to contaminating E4 or E6 in the E2 sample. For the purposes of calculating the percent of E2 isomers A and C, the sum of the mole percent of L0, L1, H1, and H2 was set to 100%.

Similarly, for E6 isomer A (for these analyses, "isomer A" refers to both isomers 6A and 6B of FIG. 7), the mole fraction of H2 is equal to the mole fraction of L1, while for E6 isomer C, the mole fractions of L0, L1, H2, and H3 are equal. Since only L0 and H3 contribute to the percentage of isomer C, the percent isomer C can be expressed as follows:

$$\% C = 2L0 + 2H3 \quad (2)$$

The percent of isomer A is assumed to be 100-% C. As with E2, the sum of the mole percent of L0, L1, H2, and H3 was set to 100%.

The percentages of the E4 isomers cannot be obtained solely from the PLRP-S HPLC data because there is not a unique solution. At least one isomer needs to be fixed before PLRP data can be used to solve for the other two isomers. The mole percent of HHL, HH, and HL were determined from Bioanalyzer data using the following molecular weights: 124,720.8 (HHL), 100,992.6 (HH), and 74,224.5 (HL) g/mol. The Bioanalyzer uses the fluorescence of bound dye for instrument readout, and it is assumed that HHL, HH, and HL bind the dye equally per unit molecule weight, although it is unlikely that this assumption is true. To minimize the error that would result from this assumption, only isomer E4A was calculated from Bioanaylzer data using the HHL, HH, and HL peak areas as follows (the HL peak area is divided by 2 since each antibody would produce 2 HL if the heavy-heavy chain disulfides were cleaved):

$$\% A = \frac{\frac{HHL}{124720.8}}{\frac{HHL}{124720.8} + \frac{HH}{100992.6} + \frac{HL}{2*74224.5}} \qquad (3)$$

PLRP-S HPLC data was then used to solve for the remaining contribution of E4 isomers E and F using the following formulas:

$$\% E = H1 + L1 - 0.5\% A \qquad (4)$$

$$\% F = H2 + L0 - 0.5\% A \qquad (5)$$

E4 isomer A contributes equally to the populations of L0, L1, H1, and H2, and the H1 and L1 contributions of isomer A (half of its total contribution) must be subtracted from the total observed amount of H1 and L1 to give the remaining amount of H1 and L1 that must be due to the presence of isomer E. A similar subtraction for the contribution of H2 and L0 for isomer A will yield the amount present due to isomer F. As with E2 and E6, the sum of the mole percent of L0, L1, H1, and H2 was set to 100%.

Example 7 of Strategies for Partial Loading of Protein

Two different strategies were used to prepare partially drug loaded ADCs. First, partial reduction of cAC10 with limiting amounts of DTT or TCEP yields fewer than 8 antibody cysteines. About 3.25 and 2.75 equivalents of DTT and TCEP, respectively, will cleave 2 interchain disulfide bonds to yield an average of 4 cAC10 cysteines per antibody (a mixture of 0, 2, 4, 6, and 8 antibody-cysteines). The amount of reducing agent can be empirically determined: cBR96 requires only 2.1 equivalents of DTT or TCEP to yield 4 antibody cysteines, while murine IgG1 antibodies can often by extremely resistant to reduction (data not shown). An advantage of using TCEP rather than DTT is that phosphines react poorly with maleimides, and any remaining reducing agent does not have to be removed before adding vcMMAE. Excess DTT readily reacts with vcMMAE and would compete with antibody-cysteines for the drug. Following antibody reduction, treatment of antibody cysteines with a slight molar excess of vcMMAE (1.1 molar equivalents per cysteine) yields cAC10 with an average drug loading of 4 MMAE per antibody (E4 mix).

Alternatively, cAC10 can be fully reduced with 10 mM DTT and then partially reoxidized with DTNB. This reoxidation process is very efficient, requiring 2.0 equivalents of DTNB to reoxidize 8 antibody cysteines to 4. Treatment of this reoxidized antibody with a thiol such as cysteine does not liberate any bound thionitrobenzoic acid, suggesting that the reoxidized cysteines are in the form of antibody disulfides rather than mixed TNB-cysteine disulfides. The analytical methods described below also show the presence of antibody disulfides. The remaining antibody cysteines can be conjugated to vcMMAE as described above to yield E4 mix.

To determine the isomeric population of each of the drug loaded species, E2, E4, and E6, are separated and isolated, yielding E2, E4, and E6 pure. FIG. 13A shows a hydrophobic interaction (HIC) HPLC trace of E4 mix made by DTT partial reduction. All of the even drug loaded species can be separated from each other, and small amounts of odd drug loaded species can be seen in the trough between the even species. The drug loading of these species can be assigned by inspection of the UV spectra of the peaks. The PABA group in the drug linker has a maximum absorbance near 248 nm, while the antibody has a minimum absorbance at the same wavelength. Using the drug and antibody extinction coefficients at 248 and 280 nm, the number of drugs per antibody can be assigned for the starting ADC mixture and each of the observed peaks (Hamblett et al. (2004), Clin Cancer Res 10: 7063-70).

Table 1 shows the percentages of the even drug loaded species prepared by DTT partial reduction, TCEP partial reduction, and partial DTNB reoxidation. The DTNB partial reduction method yields a slightly higher percentage of E4 (38%) than the partial reduction methods (30% for DTT and 33% for TCEP). This comes at the expense of mainly E6 and E8, which total about 34% for DTT partial reduction and 31% for TCEP partial reduction, while only 24% for DTNB partial reoxidation. The odd drug loaded species not shown on the table and account for 7-10% of the total material.

TABLE 1

Percent composition of E4 mixture.[a]

| Production method | E0 | E2 | E4 | E6 | E8 |
|---|---|---|---|---|---|
| DTT partial reduction | 9 ± 2 | 20 ± 3 | 30 ± 1 | 24 ± 3 | 10 ± 3 |
| TCEP partial reduction | 8 ± 1 | 20 ± 3 | 33 ± 2 | 22 ± 2 | 9 ± 1 |
| DTNB partial reoxidation | 10 ± 4 | 18 ± 3 | 38 ± 2 | 20 ± 4 | 4 ± 2 |

[a]HIC-HPLC chromatograms were integrated for percent composition. Values are plus or minus standard deviation for 4 (DTT partial reduction), 3 (TCEP partial reduction), or 6 (DTNB partial reoxidation) separate batches. The contributions from odd species are not shown, causing the total to be less than 100%.

Figure 13:
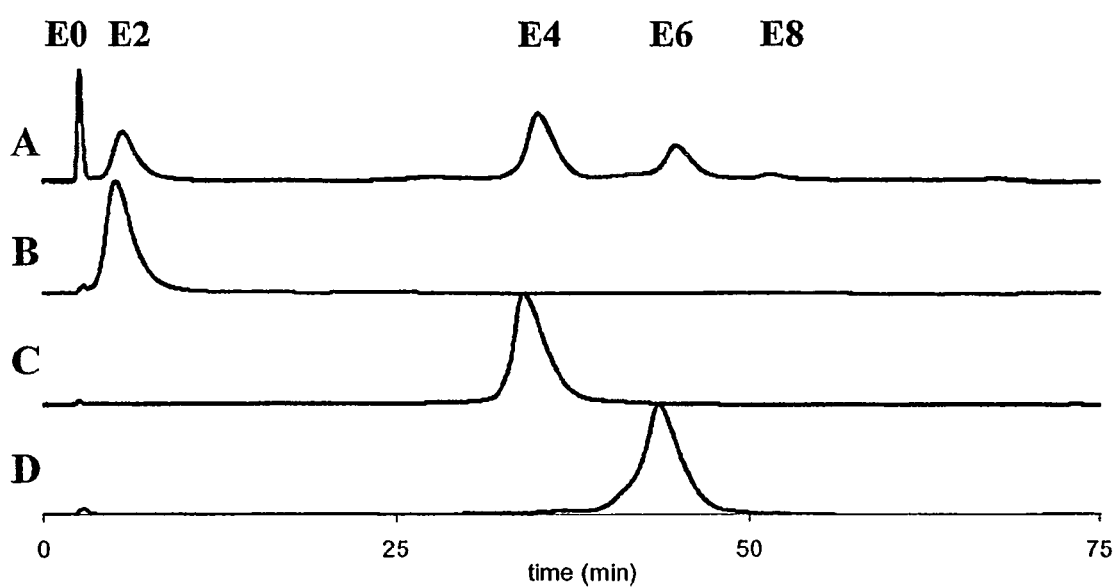
FIGS. 13A-D show hydrophobic interaction chromatography HPLC traces of (A) E4 mix; (B) E2 pure made by preparative HIC; (C) E4 pure made by preparative HIC; and (D) E6 pure made by preparative HIC, respectively. Samples were made by DTT partial reduction followed by MMAE conjugation. Chromatograms were normalized to the height of the tallest peak in each chromatogram. Injections were 50 μL of 5-10 mg/mL cAC10-vcMMAE in PBS mixed with 50 µL of 2.0 M NaCl and 50 mM sodium phosphate pH 7. Separations were performed at 30° C.
Figure 14:
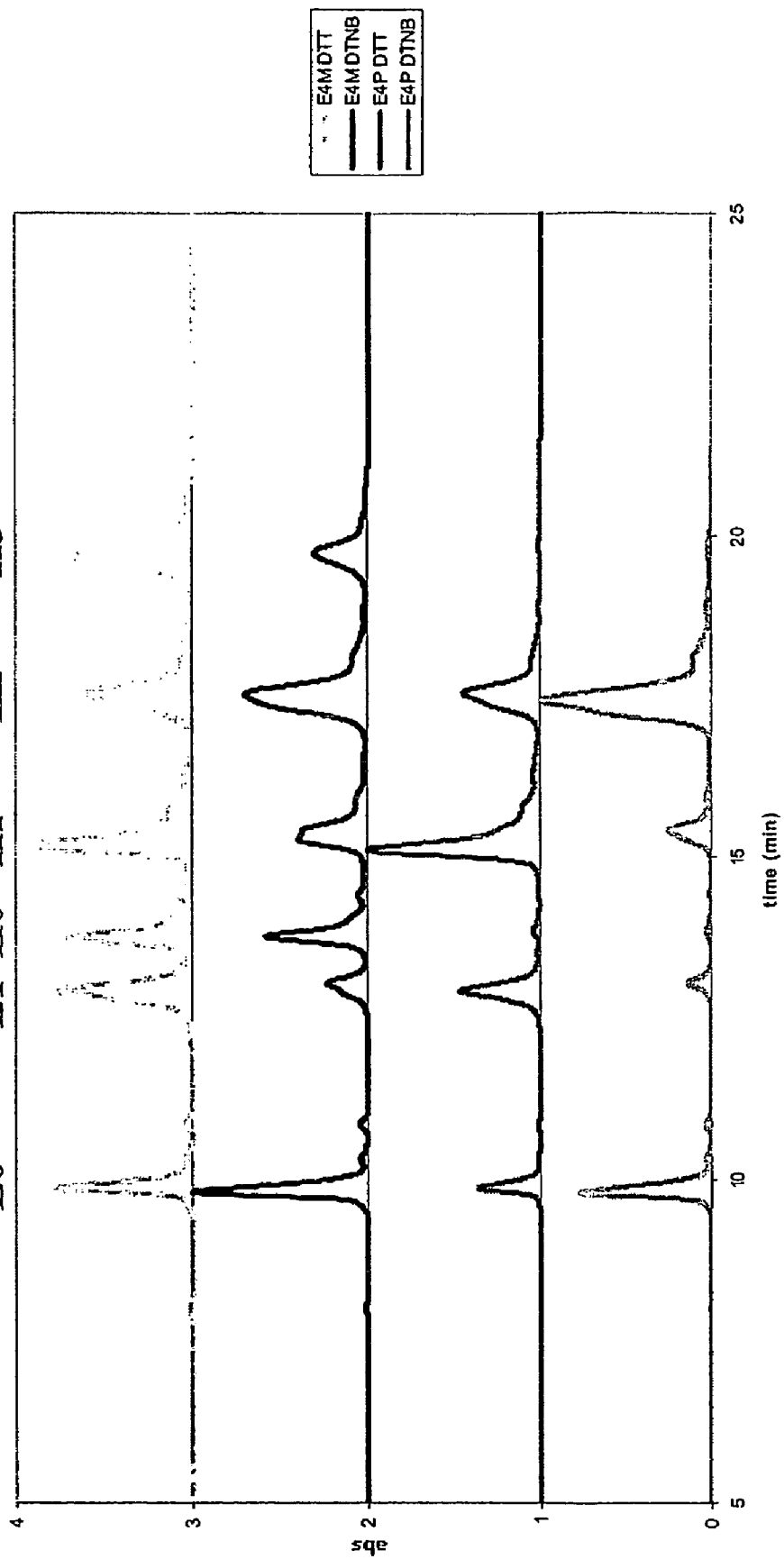
FIG. 14 show PLRP-S HPLC traces of (A) E4 mix made by partial DTT reduction followed by MMAE conjugation (top trace); (B) E4 mix made by DTNB partial reoxidation followed by MMAE conjugation (second trace from top); (C) E4 pure made by partial DTT reduction followed by MMAE conjugation and purified by preparative HIC (second trace from bottom); and (D) E4 pure made by partial DTNB reoxidation followed by MMAE conjugation and purified by preparative HIC (bottom trace). Injections were 20 µL of 1 mg/mL cAC10-vcMMAE treated with 20 mM DTT for 15 min at 37° C. Separations were performed at 80° C.

This HIC-HPLC method can be used to isolate a few milligrams of E2, E4, and E6 pure. Alternatively, preparative HIC using step gradients can be used to isolate hundreds of milligrams of E2, E4, and E6 pure, as shown in FIG. 13 B, C, D. The purity of these materials, with respect to their drug loading levels, is at least 95%.

Figure 15:
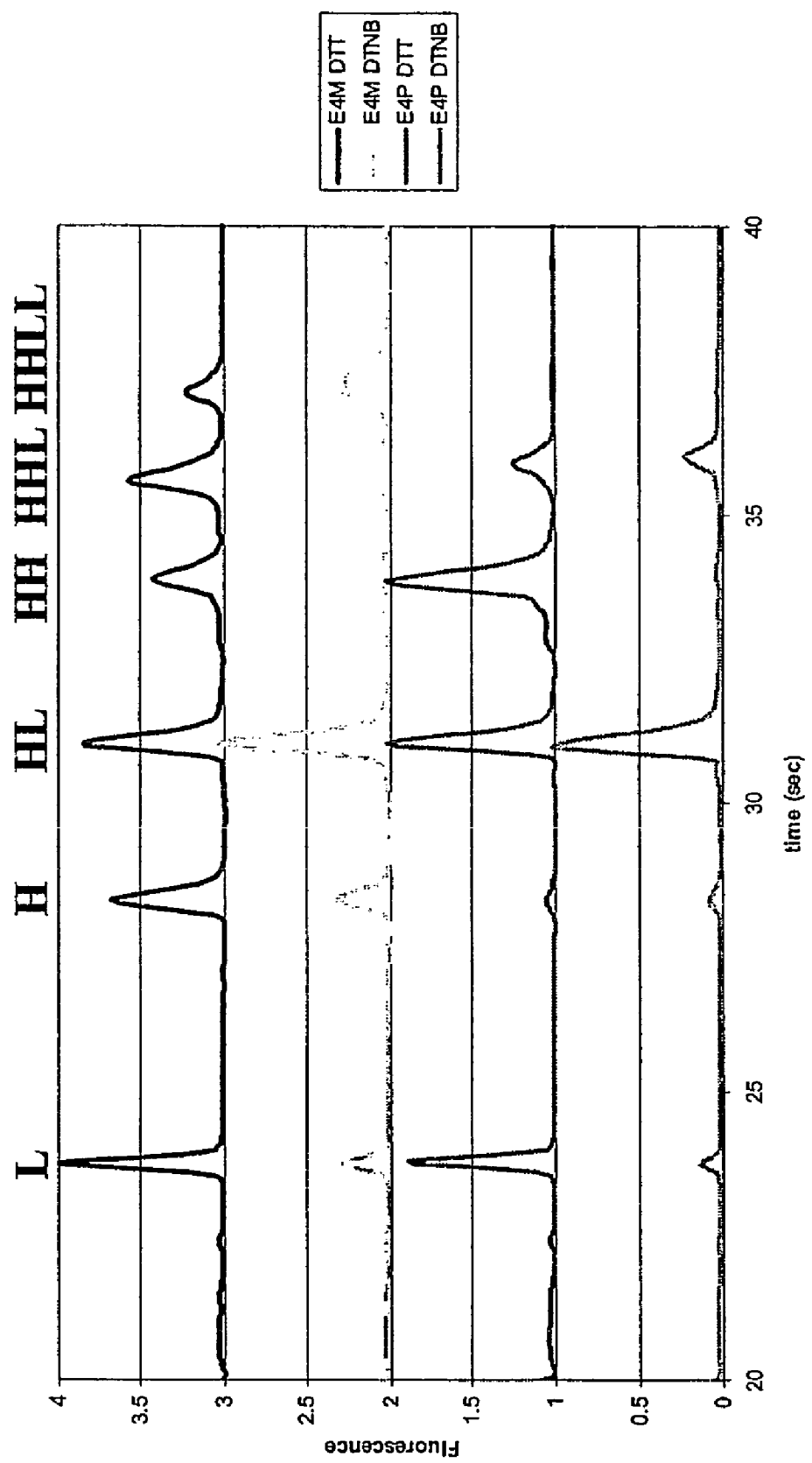
FIG. 15 shows Bioanalyzer (capillary electrophoresis) traces of (A) E4 mix made by partial DTT reduction followed by MMAE conjugation (top trace); (B) E4 mix made by DTNB partial reoxidation followed by MMAE conjugation (second trace from top); (C) E4 pure made by partial DTT reduction followed by MMAE conjugation and purified by preparative HIC (second trace from bottom); and (D) E4 pure made by partial DTNB reoxidation followed by MMAE conjugation and purified by preparative HIC (bottom trace). Samples were prepared under non-reducing conditions as directed by the manufacturer.

These purified materials were subjected to two analytical methods to determine the distribution of the drugs on the antibody (see Example 6). First, reducing and denaturing HPLC on a PLRP-S column was used to determine the number of drugs per antibody chain. Pretreatment of the ADC with an excess of DTT breaks the remaining interchain disulfides and allows separation of light chain with 0 or 1 drugs (L0 and L1) from heavy chain with 0, 1, 2, or 3 drugs (H0, H1, H2, and H3) (FIG. 4). Second, non-reducing and denaturing capillary electrophoresis allows separation of antibody chains with the remaining interchain disulfides intact, resulting in 6 potential species: L, H, HL, HH, HHL, and HHLL (FIG. 15).

Quantitation of the species observed by PLRP-S HPLC and capillary electrophoresis allows assignment of the isomeric populations. FIGS. 1 and 7 illustrate the antibody fragments and the number of associated drugs for each of the isomers. The isomeric populations of E2 and E6 can easily be determined by PLRP-S HPLC alone or capillary electrophoresis alone because each isomer yields a unique pattern. For instance, only isomer E2C yields L1 and H0 under denaturing and reducing conditions, while E2A only yields L0 and H1, and under denaturing and non-reducing conditions isomer E2A yields HHLL while E2C yields L and HHL. For E4, neither PLRP-S HPLC nor capillary electrophoresis alone is sufficient to calculate the isomeric populations, so the two methods must be used in combination to determine the composition. Table 2 shows the percent composition for each of these isomers. PLRP-S HPLC data was used exclusively for calculating the isomeric composition of the E2 and E6 isomers using Equations 1 and 2 (see Example 6). Capillary electrophoresis was used to calculate the amount of E4A using Equation 3, and PLRP-S HPLC was used to calculate the amount of E4B and E4C using Equations 4 and 5 which subtract out the contribution of E4A (see Example 6).

TABLE 2

Composition of isomeric population of purified E2, E4, and E6.

| Production method | E2A[a] | E2C[a] | E4A[b] | E4E[c] | E4F[c] | E6A[d] | E6C[d] |
|---|---|---|---|---|---|---|---|
| DTT partial reduction | 8 | 92 | 10 | 59 | 31 | 2 | 98 |
| DTNB partial reoxidation | 77 | 23 | 17 | 8 | 75 | 4 | 96 |
| AET pH 5 partial reduction | 17 | 83 | 13 | 46 | 41 | 2 | 98 |

[a]Determined from PLRP-S HPLC data using Equation 1.
[b]Determined from Bioanalyzer data using Equation 3.
[c]Determined from PLRP-S HPLC data using Equations 4 and 5.
[d]Determined from PLRP-S HPLC data using Equation 2.

The data in Table 2 is striking because the production method significantly effects the location of the drugs, suggesting that the antibody disulfides can be selectively reduced. Partial DTT reduction yields 92% isomer E2C, which results from reduction of one of the heavy-light chain disulfides, 59% isomer E4E, which results from the reduction of both heavy-light chain disulfides, and 98% isomer E6C, which results from reduction of both heavy-heavy chain disulfides and one heavy-light chain disulfide. Isomers with one heavy-heavy chain disulfide reduced are in the extreme minority. On the other hand, partial DTNB reoxidation yields almost the opposite result for E2 and E4 isomers, 77% isomer E2A and 75% E4A, where one heavy-heavy chain disulfide is intact, and the same result for E6, 96% E6C. Acidic reduction with AET yields an isomer population that is very similar to DTT partial reduction, and favors cleavage of the heavy-light chain disulfides.

The kinetics of the isomer distribution for DTT partial reduction is shown in Table 3. cAC10 was reduced with 3.0 equivalents of DTT and samples were periodically removed and alkylated with vcMMAE. E2, E4, and E6 pure were obtained by HIC-HPLC, and the isomer distribution was determined by PLRP-S HPLC and Bioanaylzer. The isomer compositions are identical over the course of the experiment, covering 10 to 120 min of reduction time and a total drug loading of 1.3 to 3.9 drugs per antibody. These results show that the DTT partial reduction isomer populations shown in Table 2, prepared by reducing cAC10 for 2 h with a limiting amount of DTT, are representative of the isomeric population over the entire course of the reduction reaction.

TABLE 3

Kinetics of isomer distribution for DTT partial reduction.

| Time (min)[a] | Drugs/mAb[b] | E2A[c] | E2C[c] | E4A[d] | E4E[e] | E4F[e] | E6A[f] | E6C[f] |
|---|---|---|---|---|---|---|---|---|
| 10 | 1.3 | 12 | 88 | 9 | 63 | 28 | N/D | N/D |
| 20 | 2.1 | 9 | 91 | 7 | 65 | 29 | 7 | 93 |
| 35 | 2.7 | 9 | 91 | 7 | 63 | 31 | 6 | 94 |
| 55 | 3.3 | 9 | 91 | 7 | 63 | 30 | 8 | 92 |
| 80 | 3.6 | 9 | 92 | 7 | 61 | 32 | 6 | 94 |
| 120 | 3.9 | 11 | 90 | 8 | 61 | 31 | 7 | 93 |

[a]Reduction time. Once reduced, all antibodies were treated with vcMMAE for identical times.
[b]Determined by HIC-HPLC.
[c]Determined from PLRP-S HPLC data using Equation 1.
[d]Determined from Bioanalyzer data using Equation 3.
[e]Determined from PLRP-S HPLC data using Equations 4 and 5.
[f]Determined from PLRP-S HPLC data using Equation 2. N/D, not determined. At this time point, very little E6 was produced and this material was not sufficient for determining the isomer population.

TABLE 4

In vitro binding and cytotoxicity of cAC10-vcMMAE.

| ADC | Binding IC$_{50}$ (µg/mL)[a] | Karpas 299 IC$_{50}$ (ng/mL)[b] |
|---|---|---|
| E0 (cAC10) | 2.70 ± 1.91 | N/D |
| E2 mix DTT | N/D | 11.4 ± 2.4 |
| E2 pure DTT | 3.57 ± 2.41 | 13.8 ± 3.6 |
| E2 mix DTNB | N/D | 11.7 ± 4.5 |
| E2 pure DTNB | 2.02 ± 1.22 | 13.2 ± 2.7 |
| E4 mix DTT | N/D | 3.4 ± 1.2 |
| E4 pure DTT | 7.76 ± 3.93 | 4.8 ± 0.7 |
| E4 mix DTNB | N/D | 5.0 ± 0.0 |
| E4 pure DTNB | 7.69 ± 4.42 | 4.3 ± 0.9 |
| E8 | 6.53 ± 3.09 | 2.7 ± 0.2 |

[a]Binding to Karpas 299, in µg of antibody component/mL, determined from 4-7 independent measurement plus or minus the standard deviation. N/D, not determined.
[b]In vitro cytotoxicity, in ng of antibody component/mL, determined from 3 independent measurements plus or minus the standard deviation. N/D, not determined. cAC10 alone displays poor potency against Karpas 299.

Table 4 lists the results of in vitro binding and cytotoxicity experiments that were performed for ADCs of several drug loading levels. E2 and E4 mix as well as E2 and E4 pure from DTT partial reduction and DTNB partial reoxidation were tested. The fully loaded conjugate with 8 drugs per antibody was the most cytotoxic, with an IC50 value on the CD30 positive Karpas 299 cell line of 2.7 ng/mL (calculated based on the weight of the antibody). The ADCs with 4 drugs per antibody were slightly less cytotoxic, with IC50 values between 3.4 and 5.0 ng/mL, and the ADCs with 2 drugs per antibody were the least cytotoxic, with IC50 values between 11.4 and 13.8 ng/mL. The chemistry used to produce the ADCs did not show any significant differences in the cytotoxicity, nor were there significant differences between the mixtures and the HIC-purified ADCs. The in vitro cytotoxicity appears to depend only on the total dose of drug. Binding to CD30 positive cells was very similar for E0, E2, and E4, with E8 being slightly impaired, demonstrating that conjugation does not interfere with antigen binding. The in vitro cytotoxicities of the ADCs (measuring the antibody component) show the expected trend: the larger the number of drugs, the lower the IC50 value. Within the error of the experiment, the location of the drugs does not appear to influence the in vitro cytotoxicity.

Example 8 of Drug Loading Effects on Antitumor Activity of Monoclonal Antibody Drug Conjugate Cells and reagents. CD30-positive ALCL line Karpas-299 was obtained from the Deutsche Sammlung von Mikroorganism und Zellkulturen GmbH (Braunschweig, Germany). L540cy, a derivative of the HD line L540 adapted to xenograft growth, was graciously provided by Dr. Harald Stein (Institut fur Pathologie, Univ. Veinikum Benjamin Franklin, Hindenburgdamm 30, 12200 Berlin, Germany). Cell lines were grown in RPMI-1640 media (Life Technologies Inc., Gaithersburg, Md.) supplemented with 10% fetal bovine serum.

Construction and purification of cAC10-Val-Cit-MMAE ADCs. Briefly, cAC10 with 8 drugs per antibody was produced by cAC10 was mixed with dithiothreitol (DTT) at 37° C. for 30 min, and the buffer was exchanged by elution through Sephadex G-25 resin with PBS containing 1 mM diethylenetriaminepentaacetic acid (DTPA). PBS containing 1 mM DTPA (PBS/D) was added to the reduced mAb (final concentration 2.5 mg/mL). A 9.5 molar excess of maleimidocaproyl-Val-Cit-MMAE, referred to as Val-Cit-MMAE, was added to the reduced antibody at 4° C. for 1 h and the conjugation reaction was quenched by adding a 20-fold excess of cysteine. The reaction mixture was concentrated by centrifugal ultrafiltration and buffer-exchanged through Sephadex G25 equilibrated in PBS at 4° C. The conjugate was then filtered through a 0.2 micron filter under sterile conditions.

The generation of cAC10 ADCs with two and four MMAE molecules per antibody involved a partial reduction followed by reaction with Val-Cit-MMAE. The antibody cAC10 (10 mg/ml) was partially reduced by addition of DTT to a final DTT:mAb molar ratio of 3.0 followed by incubation at 37° C. for ~2 h. The reduction reaction was then chilled to ~10° C. and the reduced cAC10 purified away from excess DTT via diafiltration. Following diafiltration, the thiol concentration in the partially-reduced cAC10 was determined by the DTNB (Ellman's) assay; in this manner, an average of about 2 disulfide bonds were reduced, thus exposing about 4 reduced Cys:mAb. To conjugate all of the reduced Cys, Val-Cit-cMMAE was added to a final Val-Cit-MMAE:reduced Cys molar ratio of about 1.15. The conjugation reaction was carried out in the presence of 15% v/v of DMSO and allowed to proceed at about 10° C. for about 30 min. Following the conjugation reaction, excess free Cys (2 moles of Cys per mole of Val-Cit-MMAE) was added to quench unreacted Val-Cit-MMAE to produce the Cys-Val-Cit-MMAE adduct. The Cys quenching reaction was allowed to proceed at about 10° C. for about 30 min. The Cys-quenched reaction mixture was purified and buffer-exchanged into PBS by diafiltration to obtain the partially loaded cAC10-Val-Cit-MMAE.

Preparative HIC fractionation. All chromatographic steps were performed at room temperature. A 1.6×25 cm column (~50 ml) was packed with Toyopearl Phenyl-650M HIC resin (Tosoh Bioscience, Montgomeryville, Pa.) and equilibrated with >5 column volumes of Buffer A (50 mM sodium phosphate, 2 M NaCl, pH 7.0) at a flow rate of 15 ml/min. To prepare the sample for loading onto the column, 39 ml of partially loaded cAC10-vcMMAE (12.9 mg/ml) was blended with 39 ml of Buffer A' (50 mM sodium phosphate, 4 M NaCl, pH 7.0). The sample was loaded onto the column at 10 ml/min; all subsequent steps were performed at a flow rate of 10 ml/min. Following sample loading, the column was washed with Buffer A until an $A_{280}$ baseline was achieved. cAC10-E2 was eluted and collected with a step gradient consisting of 65% Buffer A/35% Buffer B (80% v/v 50 mM sodium phosphate, pH 7.0, 20% v/v acetonitrile). After baseline was again achieved, cAC10-E4 was eluted and collected with a step gradient consisting of 30% Buffer A/70% Buffer B. Both cAC10-E2 and cAC10-E4 peaks were collected to ~20% of their respective peak heights. The fractions of interest were buffer exchanged into PBS using Ultrafree-15 centrifugal filter devices with a molecular weight cutoff of 30 kDa (Millipore, Billerica, Mass.).

Analysis of conjugates. Analysis of the conjugates was accomplished by HIC-HPLC using an Ether-5PW column (Tosoh Bioscience, Montgomeryville, Pa.). The method consisted of a linear gradient from 100% Buffer A to 100% Buffer C (80% v/v 50 mM sodium phosphate, pH 7.0, 10% v/v acetonitrile, 10% v/v isopropanol) in 50 min. The flow rate was set at 1 ml/min, the temperature was set at 30° C., and detection was followed at both 248 and 280 nm. The identity of unmodified cAC10 and cAC10-E8 peaks was confirmed by injection of cAC10 and cAC10-E8 standards. Because the antibody and drug have distinct absorbance maxima ($\lambda_{max}$=280 and 248 mm, respectively), it was possible to identify peaks corresponding to cAC10 conjugates with 2, 4, and 6 drugs per antibody by overlaying peak spectra.

In vitro characterization of cAC10-Val-Cit-MMAE ADCs. Competition binding was performed on the ADCs to determine if the conjugation or presence of drug affected the antigen binding. To compare saturation binding of mAb and ADC, 5×10$^5$ Karpas-299 cells were combined with serial dilutions of cAC10, cAC10-E2, cAC10-E4, or cAC10-E8 in the presence of 1 µg/ml cAC10 labeled with Alexa Fluor 488 (Molecular Probes, Eugene, Oreg.) in staining medium for 30 min on ice and washed twice with ice cold staining medium. Labeled cells were examined by a Fusion microplate reader (Perkin-Elmer, Boston, Mass.). Sample data were background-corrected and reported as the percent of maximum fluorescence as calculated by the sample fluorescence divided by the fluorescence of cells stained with 1 µg/mL cAC10-Alexa Fluor® 488 alone.

The growth inhibitory activities of cAC10 conjugates were determined by measuring DNA synthesis. Conjugates were incubated with CD30$^+$ Karpas-299 or L540cy cells or CD30$^-$ WSU-NHL cells. After a 92 h incubation with cAC10 or cAC10 ADCs cells were labeled with [$^3$H]-thymidine, 0.5 µCi/well, for 4 h at 37° C. Cells were harvested onto filters using a harvester, mixed with scintillation fluid and the radioactivity was measured with a Topcount scintillation counter (Packard Instruments, Meriden, Conn.). The percent untreated was plotted versus concentration for each molecule to determine the IC$_{50}$ (defined as the mAb concentration that gave 50% inhibition of DNA synthesis).

Xenograft models of human ALCL. To establish a subcutaneous disease model of ALCL 5×10$^6$ Karpas-299 cells were implanted into the right flank of CB-17 SCID mice (Harlan, Indianapolis, Ind.). Therapy with ADCs was initiated when the tumor size in each group of 6-10 animals averaged approximately 50-100 mm$^3$. Treatment consisted of either a single injection or multiple i.v. injections using the schedule of one injection every 4 days for 4 injections (q4d×4). Tumor volume was calculated using the formula (length×width$^2$)/2. A tumor that decreased in size such that it was unpalpable was defined as a complete regression (CR). A complete regression that lasted for ≧10 tumor doubling times was defined as a cure. Tumor growth inhibition (TGI) was calculated when tumors in the control group reached 750-1000 mm$^3$ in size as follows:

$$TGI = 1 - \frac{\text{(Mean tumor volume of treated group)}}{\text{(Mean tumor volume of control group)}} \times 100$$

Maximum tolerated dose. Groups of three BALB/c mice (Harlan, Indianapolis, Ind.) were injected with 30-60 mg/kg of cAC10-E8, 60-120 mg/kg of cAC10-E4, or 200-250 mg/kg of cAC10-vcMMAE2 via the tail vein to determine the single dose maximum tolerated dose (MTD). Mice were monitored daily for 14 days, and both weight and clinical observations were recorded. Mice that developed significant signs of distress were sacrificed in accordance with ACUC guidelines. The maximum tolerated dose was defined as the highest dose which did not cause a serious overt toxicities or greater than 20 percent weight loss within two weeks of injection in any of the animals.

Pharmacokinetics. The pharmacokinetics of cAC10, cAC10-E2, cAC10-E4, and cAC10-E8 were evaluated in SCID mice. SCID mice (n=3) were administered 10 mg/kg of test material (based on the antibody component) by tail vein injection. Blood samples were collected from each mouse via the saphenous vein at 1 h, 4 h, 1d, 2 d, 4 d, 7 d, 14 d, 21 d, 28 d, 35 d, 42 d, and 49 days post injection. Blood was collected into heparin coated tubes followed by centrifugation (14,000×g, 3 min) to isolate plasma. Plasma concentrations of cAC10 and ADCs were measured by ELISA.

Briefly, the ELISA consisted of the following steps: plate coat, block, sample binding, secondary mAb, TMB, and acid stop. After each step the wells were washed with wash buffer (PBS, 0.05% Tween-20, pH=7.4) three times. In the plate coat step anti-cAC10 mAb was coated onto 96-well plates at 2 µg/mL in carbonate buffer (0.1 M carbonate/bicarbonate, pH=9.6) at 4° C. overnight. Following the plate coat, blocking buffer (PBS, 1% BSA, 0.05% Tween-20) was added and incubated at room temperature for 1 h. Next, 100 µL of standard or diluted plasma sample was added to triplicate wells for 1 h at room temperature. The secondary step consisted of a mouse anti-human IgG-HRP conjugate (Southern Biotech, Birmingham, Ala.) incubated for 1 h. Subsequently, 100 µL of 3,3',5,5'-tetramethylbenzidine (Sigma, St. Louis, Mo.) was added to each well and upon color development the reaction was stopped with 100 µL of 1 N sulfuric acid. Optical density was measured using a VMax Kinetic Microplate reader (Molecular Devices, Sunnyvale, Calif.) at 450 nm and a blank at 630 nm. Non-compartmental pharmacokinetic parameters were calculated with WinNonlin (Pharsight, Mountain View, Calif.).

Figure 10:
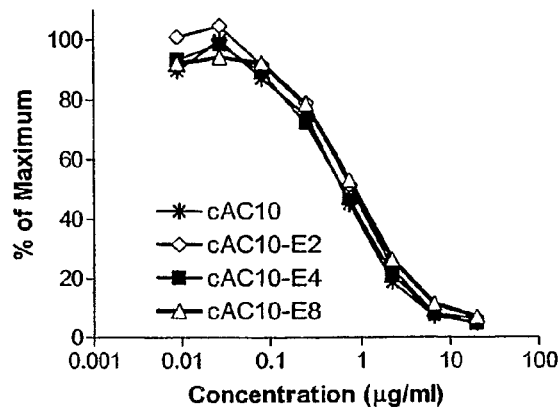
FIG. 10 shows a graph of the internalization of cAC10-conjugated antibody by $CD30^+$ Karpas-299 cells. The cells were combined with 1 μg/mL of fluorescently-labeled cAC10 and serial dilutions of either cAC10, cAC10-E2, cAC10-E4, or cAC10-E8 from 20 μg/mL to 9 ng/mL. After incubation of the cells with the antibody, the labeled cells were washed with staining media, and the fluorescence was measured. The normalized fluorescence intensities were plotted versus mAb concentration as described in Example 8.

In vitro characterization. Competition binding experiments were performed to evaluate if conjugation of MMAE to cAC10 interfered with the CD30 binding capability of the ADCs. CD30+ Karpas-299 cells were incubated with 1 µg/mL of fluorescently labeled cAC10 combined with serial dilutions of unlabeled antibody, cAC10-E2, cAC10-E4, or cAC10-E8. As shown in FIG. 10, each of the ADC variants effectively competed with fluorescently labeled cAC10 equivalent to unlabeled cAC10. Thus, conjugation with MMAE did not reduce antigen binding.

Figure 11A:
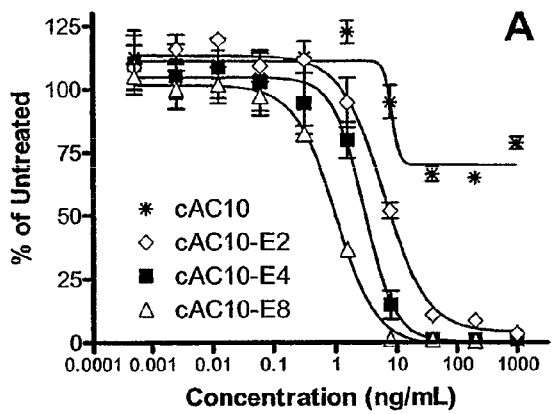
FIGS. 11A and 11B show graphs of the internalization of cAC10 and cAC10-conjugated antibodies by $CD30^+$ cells: A) Karpas-299 and B) L540cy cells were incubated with serial dilutions of cAC10 and E2, E4 and E8 species of cAC10 ADCs. Following a 96-hour incubation with the samples, $[^3H]$-TdR was added and its incorporation was measured. The radioactivity of the treated samples was normalized to the untreated controls and plotted versus concentration.
Figure 11:
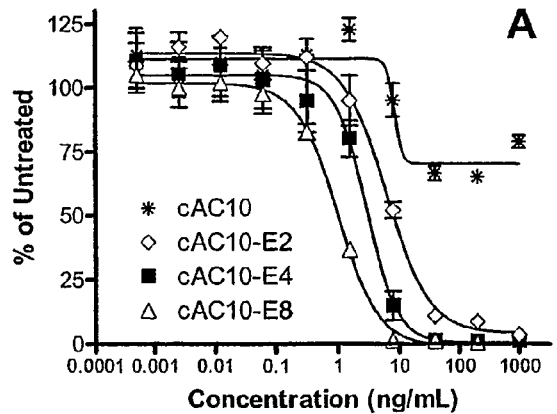

The in vitro cytotoxic activities of the ADCs were evaluated by a [$^3$H]-TdR incorporation assay with CD30+ Karpas-299 and L540cy cells and CD30− WSU-NHL cells. cAC10-E8 demonstrated significant activity against the Karpas-299 cells with an $IC_{50}$ of 1.0 ng/mL (FIG. 11$a$). Decreasing the amount of drug in half to four MMAE molecules per mAb (cAC10-E4) increased the $IC_{50}$ to 2.9 ng/mL. Halving the drug loading again further increased the $IC_{50}$ to 6.2 ng/mL with cAC10-E2. Against the HD line L540cy the ADCs had a similar trend with $IC_{50}$ values of 1.4, 4.5, and 9.2 ng/mL for cAC10-E8, cAC10-E4, and cAC10-E2, respectively (FIG. 11$b$). Selectivity of the ADCs was evaluated with CD30− WSU-NHL cell line which were insensitive to all cAC10-ADCs with $IC_{50}$ values >1000 ng/ml (data not shown).

Xenograft models of human ALCL. The effect of drug loading on in vivo anti-tumor activity was evaluated with a Karpas-299 subcutaneous xenograft models. Therapy was administered every fourth day for a total of 4 injections (q4dx 4) starting when tumor volumes reached 50-100 mm$^3$. Using this schedule, it was previously found that cAC10-E8 at 1 mg/kg produced 100% CRs, at the same dose cAC10-E4 obtained 100% CRs (data not shown). With the goal of comparing the activity of the ADCs, lower doses were used for cAC10-E4 and cAC10-E8. Cohorts of mice bearing subcutaneous Karpas-299 xenografts were treated with multiple doses of cAC10-E2 (0.5 mg/kg/dose or 1 mg/kg/dose), cAC10-E4 (0.25 or 0.5 mg/kg/dose), or cAC10-E8 (0.25 or 0.5 mg/kg/dose). Table 5 displays a summary of the efficacy results.

TABLE 5

| Schedule | ADC | Dose (mg/kg) | Complete Regressions | Cures | TGI |
|---|---|---|---|---|---|
| q4dx4 | cAC10-E2 | 0.5 | 0/10 | 0/10 | 68% |
|  |  | 1.0 | 10/10 | 10/10 | 97% |
|  | cAC10-E4 | 0.25 | 1/10 | 1/10 | 56% |
|  |  | 0.50 | 5/10 | 3/10 | 91% |
|  | cAC10-E8 | 0.25 | 0/10 | 0/10 | 47% |
|  |  | 0.50 | 6/10 | 6/10 | 90% |
| x1 | cAC10-E2 | 1.0 | 4/6 | 4/6 | 96% |
|  | cAC10-E4 | 1.0 | 6/6 | 5/6[a] | 100% |
|  | cAC10-E8 | 1.0 | 5/6 | 5/6 | 100% |
| x1 | cAC10-E4 | 1.0 | 9/10 | 7/10 | 99.2% |
|  | cAC10-E4-Mixture | 1.0 | 8/10 | 8/10 | 98.4% |

Table 5: Anti-tumor activity of cAC10-E2, cAC10-E4, cAC10-E4-Mixture, and cAC10-E8 in a subcutaneous Karpas-299 xenograft model. Animals were treated with ADCs once tumor volumes reached 50-100 mm$^3$. Doses were given once (x1) or four times every four days (q4dx4). The number of complete regressions, cures and tumor growth inhibition (TGI) are reported. [a]one mouse with a cure was found dead on Day 72 with no sign of tumor mass.

Figure 12A:
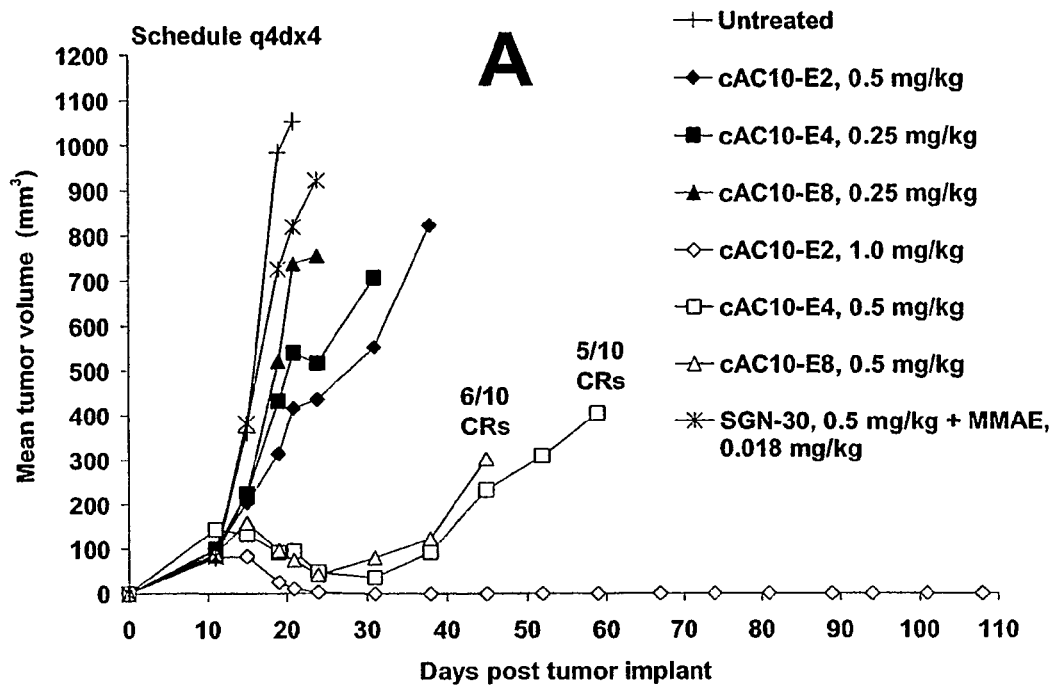
FIGS. 12A and 12B show in vivo efficacy cAC10 and cAC10-conjugated antibodies in SCID mice bearing subcutaneous xenografts.

While cAC10-E8 had twice the amount of MMAE as cAC10-E4 at the same mAb dose, they were equally effective at both dose levels (FIG. 12A). At the 0.5 mg/kg/dose, out of the ten animals treated with cAC10-E4 five achieved complete regressions (CRs) and cAC10-E8 induced six often CRs. Untreated tumors reached a mean tumor volume of 986 mm$^3$ 19 days following implant. Tumor growth inhibition of cAC10-E4 was 91% compared to 90% for cAC10-E8. At 0.25 mg/kg/dose both of these ADCs induced a similar delay in tumor growth compared to untreated control animals but no complete regressions. cAC10-E2 at 1.0 mg/kg/dose, a dose which contained the same amount of MMAE as cAC10-E4 at 0.5 mg/kg/dose and cAC10-E8 at 0.25 mg/kg, induced 10/10 cures. The effect on tumor growth with cAC10-E2 at 0.5 mg/kg/dose was comparable to that seen with cAC10-E4 and cAC10-E8 at 0.25 mg/kg/dose generating a TGI of 68%. A physical mixture of the drug MMAE with cAC10, equivalent to cAC10-E8 at the 0.5 mg/kg dose, produced only a slight delay in tumor growth compared to untreated, highlighting that the linkage of drug to antibody is critical for achieving anti-tumor activity.

Figure 12B:
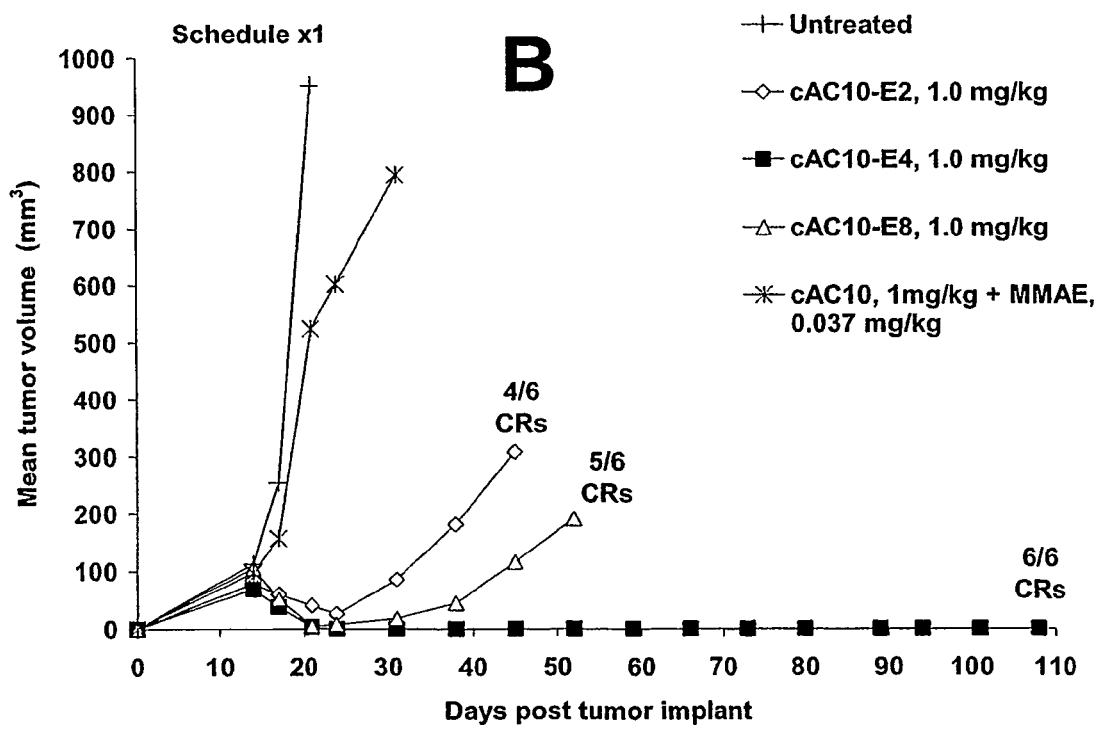

Single dose treatment of cAC10-E2, cAC10-E4, and cAC10-E8 in this same model were then compared at 1.0 mg/kg (FIG. 12B). Five of six animals treated with cAC10-E8 achieved cures. Of the six animals treated with cAC10-E4 all achieved complete regressions with five cures out to 108 days, the end of the study, one animal was found dead on day 72 with no sign of tumor mass. Even though cAC10-E2 at 1.0 mg/kg contained half as much MMAE as cAC10-E4 four of six mice achieved CRs. The control group consisting of 1 mg/kg of cAC10 plus 0.037 mg/kg free MMAE, equivalent to the amount of drug contained in 1 mg/kg of cAC10-E8, had little effect on tumor growth compared to untreated mice.

The initial conjugation of the partially-loaded ADC resulted in a mixture of species containing 0-8 drugs/mAb. To evaluate the activity of this mixture (cAC10-E4-Mixture) single dose anti-tumor activity of cAC10-E4-Mixture was compared to the purified cAC10-E4 at 1.0 mg/kg. Similar to the previous single dose experiment nine of ten mice treated with cAC10-E4 achieved CRs. Complete regression were generated in eight of ten mice treated with cAC10-E4-Mixture, with an average molar ratio of 4.0. Although it contained a population of ADCs with different drug loadings the partially loaded cAC10-E4-Mixture demonstrated equivalent anti-tumor activity to the purified cAC10-E4.

Maximum tolerated dose and therapeutic window. The single-dose tolerability of cAC10-E2, cAC10-E4, and cAC10-E8 was evaluated in BALB/c mice with three per group. The maximum tolerated dose (MTD) was defined as the highest dose that did not induce greater than 20% weight loss or severe signs of distress or overt toxicities in any of the animals. For cAC10-E8, mice were dosed at 10 mg/kg intervals from 30-60 mg/kg. At a dose of 50 mg/kg, mice had a maximum weight loss of 14% six days after injection, after which the weight loss recovered. A dose of 60 mg/kg induced 23% weight loss six days post injection in one animal. With cAC10-E4 at 100 mg/kg, mice reached a maximum weight loss of approximately 10%. At 120 mg/kg of cAC10-E4 one animal displayed signs of significant distress and 17% weight loss and the animal was euthanized. Mice treated with cAC10-E2 at doses up to 250 mg/kg, the highest dose tested, experienced a maximum weight loss of 10.5% 6 days post injection, with no signs of distress. Based on our observations, the MTD of cAC10-E2 was at least 250 mg/kg, cAC10-E4 was 100 mg/kg, and cAC10-E8 was 50 mg/kg. Therapeutic index was defined as ratio of the single dose MTD to the multi-dose efficacious dose, yielding 100 for cAC10-E8, 200 for cAC10-E4, and at least 250 for cAC10-E2.

Pharmacokinetics. SCID mice were administered with cAC10, cAC10-E2, cAC10-E4, and cAC10-E8 to determine how drug loading effects pharmacokinetics. Table 6 illustrates the pharmacokinetic parameters established by non-compartmental analysis.

TABLE 6

Pharmacokinetic parameters of cAC10 and cAC10 ADCs in SCID mice at a dose of 10 mg/kg. The half-life (t½), area under the curve (AUC), clearance (CL), volume of distribution (Vz), and area under the curve from injection to day 14 (AUC t(0-14 d)) were calculated using non-compartmental analysis.

| Name | t½ (days) | AUC (µg-day/mL) | CL (mL/day/kg) | Vz (mL/kg) |
|---|---|---|---|---|
| cAC10 | 16.7 | 2638 | 3.8 | 91 |
| cAC10-E2 | 16.9 | 2313 | 4.4 | 107 |
| cAC10-E4 | 14.0 | 1689 | 6.0 | 121 |
| cAC10-E8 | 14.9 | 520 | 19.2 | 414 |

The time-concentration curves of cAC10, cAC10-E2, cAC10-E4, and cAC10-E8 followed bi-exponential declines. The terminal half-lives were 16.7, 16.9, 14.0 and 14.7 days, respectively and thus, did not directly correlate with drug loading. However, the exposure of ADCs as determined by the AUC increased as drug loading decreased, ranging from 2638 µg-day/mL for unmodified cAC10 to 520 µg-day/mL for cAC10-E8. Conversely, the clearance values increased from 3.8 mL/day/kg for cAC10 to 4.4, 6.0 and 19.2 mL/day/kg for cAC10-E2, cAC10-E4, and cAC10-E8, respectively. Similarly, the volume of distribution was found to directly correlate to drug loading.

Example 9 of Further Study of in Vivo Efficacy

In vivo efficacy experiments were performed using the Karpas 299 CD30 positive cell line and are shown in Table 7. Subcutaneous Karpas-299 tumors were grown in C.B.-17 SCID mice, with the test articles administered when tumors reached approximately 100 mm$^3$ (length×width$^2$). Animals were separated into groups of 5-10 animals, and each group was injected with ADC intravenously. Doses were made in 2-fold serial dilutions (0.5, 1.0 2.0 mg/Kg) and tumors that regressed to an unmeasurable size were defined as complete remissions. The dose that yielded ≧80% complete remissions over several experiments (3-8, with 5-15 animals per dose except E6P, which was a single group of 4 animals) was assigned as the efficacious dose. For all the ADCs tested, the efficacious dose was 1 mg/Kg, despite the fact that the amount of injected drug component changed with the drug loading. Within the precision of the experiment (2-fold serial dilutions), the isomeric distribution of the drugs did not influence the efficacy.

To evaluate the tolerability of the ADCs BALB/c mice (parent strain of the C.B.-17 SCID) were administered with ADCs. Animal weights were measured and clinical observations were recorded over a 14 day period. The MTD was assigned as the highest single dose administered to a BALB/c mouse that did not result in weight loss ≧20% or show signs of distress. For E8, doses were 40, 50 and 60 mg/Kg, for E4, doses were 80, 100 and 120 mg/Kg, and for E2, doses were 200 and 250 mg/Kg. As observed previously (see Example 8), the absolute drug loading level did influence the MTD, with higher drug loading levels having lower MTD values. For E4 pure made by DTNB partial reoxidation, the MTD was slightly higher than for E4 pure made by the DTT partial reduction (120 versus 100 mg/Kg).

TABLE 7

Mouse in vivo efficacy on CD30$^+$ Karpas 299 cells and MTD for cAC10- vcMMAE.

| ADC | Efficacious dose (mg/Kg)$^a$ | MTD (mg/Kg)$^a$ |
|---|---|---|
| E2P DTT | 1 | >250 |
| E4P DTT | 1 | 100 |
| E4P DTNB | 1 | 120 |
| E6P DTT | 1 | 80 |
| E8 | 1 | 50 |

$^a$In vivo doses were based on mg of antibody component per Kg of body weight.

No license is expressly or implicitly granted to any patent or patent applications referred to or incorporated herein. The discussion above is descriptive, illustrative and exemplary and is not to be taken as limiting the scope defined by any appended claims.

Various references, including patent applications, patents, and scientific publications, are cited herein, the disclosures of each of which is incorporated herein by reference in its entirety.

What is claimed is:

1. A method of conjugating a drug to an antibody, comprising:
   fully reducing the antibody with a reducing agent;
   treating the fully reduced antibody with limiting amounts of a reoxidizing agent to reform at least one interchain disulfide bond of the antibody to form a partially reoxidized antibody, such that at least two cysteine thiols from the interchain thiols remain; and
   conjugating the drug to an interchain thiol of the partially reoxidized antibody via a maleimide group.

2. The method of claim 1, wherein the reoxidizing agent is 5,5'-dithio-bis-2-nitrobenzoic acid, 4,4'-dithiodipyridine, 2,2'-dithiodipyridine, sodium tetrathionate or iodosobenzoic acid.

3. The method of claim 2, wherein the drug is a cytotoxic or cytostatic agent or an immunosuppressive agent.

4. The method of claim 3, wherein the cytotoxic or cytostatic agent is a minor grove binder, an ester produced by reacting auristatin E with paraacetyl benzoic acid (AEB), an ester produced by reacting auristatin E with benzoylvaleric acid (AEVB), dovaline-valine-dolaisoleunine-dolaproine-phenylalanine (MMAF), monomethyl auristatin E (MMAE), or dimethylvaline-valine-dolaisoleunine-dolaproine-phenylalanine-p-phenylenediamine (AFP).

5. The method of claim 1, wherein at least two drugs are conjugated to the partially reoxidized antibody and each drug is conjugated to a distinct interchain thiol.

6. The method of claim 1, wherein the reducing agent is DTT or TCEP.

7. The method of claim 1, further comprising purifying the partially reoxidized antibody.

8. A method of producing a conjugated antibody comprising:
   contacting an antibody solution with a large excess of a reducing agent and incubating the resulting solution at about 37° C. for about 30 minutes, to produce a fully reduced antibody;
   purifying the fully reduced antibody using column chromatography, dialysis or diafiltration;
   partially reoxidizing the fully reduced antibody using an oxidizing agent to form at least one interchain disulfide bond by
      cooling the fully reduced antibody to about 0° C.;
      treating the fully reduced and cooled antibody with 1.5 to 2.5 molar equivalents of the oxidizing agent to form a reaction solution;
      mixing the reaction solution by inversion;
      allowing the reaction solution to incubate at about 0° C. for about 10 to 20 minutes and produce a partially reoxidized antibody;
   purifying the partially reoxidized antibody;
   conjugating a drug to a cysteine thiol from an interchain thiol of the partially reoxidized antibody via a maleimide group to form the conjugated antibody; and
   purifying the conjugated antibody.

9. The method of claim 8, wherein at least two drugs are conjugated to the antibody and each drug is conjugated to an interchain thiol.

10. A method of preparing a mixture of antibody drug conjugates, comprising:
    fully reducing antibodies with a reducing agent to form fully reduced antibodies;
    partially reoxidizing the fully reduced antibodies with limiting amount of a reoxidizing agent to form partially reoxidized antibodies; and
    conjugating a drug to an interchain thiol of the partially reoxidized antibodies via a maleimide group to form antibody drug conjugates, wherein the average number of drugs per antibody in the mixture of antibody drug conjugates is less than the number of interchain thiols present on the fully reduced antibodies.

11. The method of claim 8, wherein the oxidizing agent is 5,5'-dithio-bis-2-nitrobenzoic acid, 4,4'-dithiodipyridine, 2,2'-dithiodipyridine, sodium tetrathionate or iodosobenzoic acid.

12. The method of claim 8, wherein the drug is a cytotoxic or cytostatic agent or an immunosuppressive agent.

13. The method of claim 12, wherein the cytotoxic or cytostatic agent is a minor grove binder, AEB, AEVB, MMAF, MMAE, or AFP.

14. The method of claim 8, wherein at least two drugs are conjugated to the conjugated antibody and each drug is conjugated to an interchain thiol.

15. The method of claim 8, wherein the reducing agent is DTT or TCEP.

16. The method of claim 10, wherein the reoxidizing agent is 5,5'-dithio-bis-2-nitrobenzoic acid, 4,4'-dithiodipyridine, 2,2'-dithiodipyridine, sodium tetrathionate or iodosobenzoic acid.

17. The method of claim 10, wherein the drug is a cytotoxic or cytostatic agent or an immunosuppressive agent.

18. The method of claim 17, wherein the cytotoxic or cytostatic agent is a minor grove binder, AEB, AEVB, MMAF, MMAE, or AFP.

19. The method of claim 10, further comprising purifying the plurality of partially reoxidized antibodies prior to conjugation with the drug.

20. The method of claim 10, wherein the reducing agent is DTT or TCEP.

21. The method of claim 10, wherein the mixture of antibody drug conjugates comprises antibodies conjugated to two drugs, antibodies conjugated to four drugs, and antibodies conjugated to six drugs.

22. The method of claim 10, wherein the average number of drugs per antibody in the mixture of antibody drug conjugates is two.

23. The method of claim 10, wherein the average number of drugs per antibody in the mixture of antibody drug conjugates is four.

24. The method of claim 1, wherein the drug is MMAE and is conjugated to the partially reoxidized antibody via a maleimidocaproyl-valine-citrulline linker.

25. The method of claim 8, wherein the drug is MMAE and is conjugated to the partially reoxidized antibody via a maleimidocaproyl-valine-citrulline linker.

26. The method of claim 10, wherein the drug is MMAE and is conjugated to the partially reoxidized antibodies via a maleimidocaproyl-valine-citrulline linker.

* * * * *